United States Patent
Woska, Jr. et al.

(10) Patent No.: US 6,846,643 B2
(45) Date of Patent: Jan. 25, 2005

(54) METHODS AND MOLECULES USEFUL FOR IDENTIFYING MOLECULES THAT BIND LFA-1 AND FOR DETERMINING RECEPTOR OCCUPANCY

(75) Inventors: Joseph R. Woska, Jr., Yorktown Heights, NY (US); Robert Rothlein, Greensboro, NC (US); Rene M. Lemieux, Plantsville, CT (US); Hans C. Reiser, New York, NY (US); Gary O. Caviness, Danbury, CT (US); Takashi Kishimoto, Lexington, MA (US); Kathleen Last-Barney, Mamaroneck, NY (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 46 days.

(21) Appl. No.: 09/922,932

(22) Filed: Aug. 6, 2001

(65) Prior Publication Data

US 2002/0068305 A1 Jun. 6, 2002

Related U.S. Application Data

(60) Provisional application No. 60/225,327, filed on Aug. 14, 2000.

(51) Int. Cl.$^7$ .............................................. G01N 33/53
(52) U.S. Cl. ...................................... 435/7.24; 424/9.2
(58) Field of Search .......................... 424/9.2; 435/7.24

(56) References Cited

PUBLICATIONS

Argenbright, L.W. et al, "Monoclonal antibodies to the leukocyte membrane CD18 glycoprotein complex and to intercellular adhesion molecule–1 inhibit leukocyte–endothelial adhesion in rabbits", Journal of Leukocyte Biology, 1991, vol. 49, pp. 253–257.

Harlow, E. et al, "Antibodies: a laboratory manual", 1988, Cold Spring Harbor Laboratory, pp. 567–569, 583 and 590. See especially p. 567, first paragraph and p. 590, first two paragraphs.

*Primary Examiner*—David Saunders
(74) *Attorney, Agent, or Firm*—Robert P. Raymond; Susan K. Pocchiari; Mary-Ellen M. Devlin

(57) ABSTRACT

The present invention relates generally to a method for identifying molecules that bind the R7.1 epitope of LFA-1 or bind LFA-1 such that the R7.1 epitope is modified. The present invention further relates to a method for determining occupancy of the LFA-1 receptor by molecules that bind to the R7.1 epitope or bind LFA-1 such that the R7.1 epitope is modified after administration to a subject. The present invention further relates to molecules useful in the methods of the invention.

9 Claims, 3 Drawing Sheets

METHODS AND MOLECULES USEFUL FOR IDENTIFYING MOLECULES THAT BIND LFA-1 AND FOR DETERMINING RECEPTOR OCCUPANCY

RELATED APPLICATIONS

This application claims benefit to U.S. Provisional Application Ser. No. 60/225,327 filed Aug. 14, 2000.

FIELD OF THE INVENTION

The present invention relates generally to a method for identifying molecules that bind or modify the R7.1 epitope of LFA-1. R7.1 is an anti-CD11a monoclonal antibody (mAb). The present invention further relates to a method for determining occupancy of the LFA-1 receptor by molecules that bind to the R7.1 epitope after administration to a subject. The invention further relates to molecules useful in such methods.

BACKGROUND OF THE INVENTION

Research spanning the last decade has helped to elucidate the molecular events attending cell-cell interactions in the body, especially those events involved in the movement and activation of cells in the immune system. See generally, Springer, T., 1990, Nature 346:425–434. Cell surface proteins, and especially the Cellular Adhesion Molecules ("CAMs") and "Leukointegrins", including LFA-1, MAC-1 and gp150.95 (referred to in WHO nomenclature as CD18/CD11a, CD18/CD11b, and CD18/CD11c, respectively) have correspondingly been the subject of pharmaceutical research and development having as its goal the intervention in the processes of leukocyte extravasation to sites of injury and leukocyte movement to distinct targets. For example, it is presently believed that prior to the leukocyte extravasation, which is a mandatory component of the inflammatory response, activation of integrins constitutively expressed on leukocytes occurs and is followed by a tight ligand/receptor interaction between integrins (e.g., LFA-1) and one or several distinct intercellular adhesion molecules (ICAMs) designated ICAM-1, ICAM-2, ICAM-3 or ICAM-4 which are expressed on leukocytes. ICAM-1, ICAM-2, and ICAM-3 are expressed on blood vessel endothelial cell surfaces, as well. The interaction of the CAMs with the Leukointegrins is a vital step in the normal functioning of the immune system. Immune processes such as antigen presentation, T-cell mediated cytotoxicity and leukocyte extravasation all require cellular adhesion mediated by ICAMs interacting with the Leukointegrins. See generally, Kishimoto, T. K. and R. R. Rothlein, 1994 Adv. Pharmacol. 25:117≧138.

A group of individuals has been identified which lack the appropriate expression of Leukointegrins, a condition termed "Leukocyte Adhesion Deficiency" (Anderson, D. C. et al., 1985, Fed. Proc, 44:671≧2677 and Anderson, D. C. et al., 1985, J. Infect. Dis., 152:668–689). These individuals are unable to mount a normal inflammatory and/or immune response(s) due to an inability of their cells to adhere to cellular substrates. These data show that immune reactions are mitigated when lymphocytes are unable to adhere in a normal fashion due to the lack of functional adhesion molecules of the CD18 family. By virtue of the fact that LAD patients who lack CD18 cannot mount an inflammatory response, it is believed that antagonism of CD18, CD11/ICAM-1 interactions will also inhibit an inflammatory response.

It has been demonstrated that the antagonism of the interaction between the CAMs and the Leukointegrins can be realized by agents directed against either component. Specifically, blocking of the CAMs, such as for example ICAM-1, or the Leukointegrins, such as for example LFA-1, by antibodies directed against either or both of these molecules effectively inhibits inflammatory responses. In vitro models of inflammation and immune response inhibited by antibodies to CAMs or Leukointegrins include antigen or mitogen-induced lymphocyte proliferation, homotypic aggregation of lymphocytes, T-cell mediated cytolysis and antigen-specific induced tolerance. See generally, Kishimoto, T. K. and R. R. Rothlein, 1994, Adv. Pharmacol. 25:117–138. The relevance of the in vitro studies are supported by in vivo studies with antibodies directed against ICAM-1 or LFA-1. See generally, Rothlein, R. and J. R. Jaeger, 1996, In Therapeutic Immunology (eds) Austen et al. Blackwell Science, Cambridge Mass., p. 347. For example, antibodies directed against LFA-1 can prevent thyroid graft rejection and prolong heart allograft survival in mice (Gorski, A., 1994, Immunology Today 15:251–255). Of greater significance, antibodies directed against ICAM-1 have shown efficacy in vivo as anti-inflammatory agents in human diseases such as renal allograft rejection and rheumatoid arthritis (Rothlein, R. R.; Scharschmidt, L., in: Adhesion Molecules; Wegner, C. D., Ed.; 1994, 1–38, Cosimi, C. B.; et al., J. Immunol. 1990, 144, 4604–4612 and Kavanaugh, A.; et al., Arthritis Rheum. 1994, 37: 992–1004) and antibodies directed against LFA-1 have demonstrated immunosuppressive effects in bone marrow transplantation and in the prevention of early rejection of renal allografts (Fischer, A. et al., Lancet, 1989, 2:1058–1060 and Le Mauff, B.; et al., Transplantation, 1991, 52:291–295).

It has also been demonstrated that a recombinant soluble form of ICAM-1 can act as an inhibitor of the ICAM-1 interaction with LFA-1. Soluble ICAM-1 acts as a direct antagonist of CD18, CD11/ICAM-1 interactions on cells and shows inhibitory activity in in vitro models of immune response such as the human mixed lymphocyte response, cytotoxic T cell responses and T cell proliferation from diabetic patients in response to islet cells (Becker, J. C.; et al., J. Immunol. 1993, 151:7224 and Roep, B. O.; et al., Lancet, 1994, 343:1590).

In addition, several small molecules have been described in the literature which affect the interaction of CAMs and Leukointegrins. A natural product isolated from the root of Trichilia rubra was found to be inhibitory in an in vitro cell binding assay (Musza, L. L.; et al., Tetrahedron, 1994, 50:11369–11378). One series of molecules (Boschelli, D. H.; et al., J. Med. Chem. 1994, 37: 717 and Boschelli, D. H.; et al., J. Med. Chem. 1995, 38: 4597–4614) was found to be orally active in a reverse passive Arthus reaction, an induced model of inflammation that is characterized by neutrophil accumulation (Chang, Y. H.; et al., Eur. J. Pharmacol. 1992, 69: 155–164). Another series of molecules was also found to be orally active in a delayed type hypersensitivity reaction in rats (Sanfilippo, P. J.; et al., J. Med. Chem. 1995, 38: 1057–1059). All of these molecules appear to act nonspecifically, either by inhibiting the transcription of ICAM-1 along with other proteins or act intracellularly to inhibit the activation of the Leukointegrins by an unknown mechanism. None of the molecules directly antagonize the interaction of the CAMs with the Leukointegrins.

Thus, the prior art has demonstrated that molecules which antagonize the binding of the CAMs to the Leukointegrins have therapeutic potential in mitigating inflammatory and immunological responses often associated with the pathogenesis of many autoimmune or inflammatory diseases.

Recently, a small molecule, (R)-5-(4-bromobenzyl)-3-(3,5-dichlorophenyl)-1,5-dimethylimidazolidine-2,4-dione (referred to herein as Compound 1), has been shown to interact specifically with LFA-1 via noncovalent binding to the CD11a chain and prevent LFA-1 from binding to ICAM-1. (Kelly et al., 1999, *J. Immunol.* 163:5173–5177).

Based on the status of the prior art, there remains a clear need for a method of identifying molecules that specifically bind or modify LFA-1. In addition, there is a need in the clinic for a method for determining LFA-1 receptor occupancy on target cells of a subject treated with such molecules for determining, inter alia: how much compound has reached target cells after treatment; the amount of compound necessary to saturate LFA-1 receptors; and how much receptor occupancy is needed for efficacy.

SUMMARY OF THE INVENTION

A first aspect of the invention comprises a method for identifying a molecule that specifically binds the R7.1 epitope of LFA-1 or binds LFA-1 such that the R7.1 epitope is modified wherein the LFA-1 is either purified or cell surface LFA-1. A second aspect of the invention comprises a method for determining LFA-1 receptor occupancy on target cells of a subject treated with a molecule that specifically binds the R7.1 epitope of LFA-1 or binds LFA-1 such that the R7.1 epitope is modified. A third aspect comprises molecules useful in the methods of the invention.

In specific embodiments, the target cells are peripheral blood mononuclear cells and polymorphonuclear leukocytes. One advantage of the cellular assays is the abrogation of the need to purify LFA-1 thereby providing a system that more closely resembles that found in nature. The methods for determining receptor occupancy described herein can provide invaluable information in the clinic for determining, inter alia: how much compound has reached target cells after treatment; the amount of compound necessary to saturate LFA-1 receptors; and how much receptor occupancy is needed for efficacy.

The invention provides methods for identifying a molecule that binds or modifies the R7.1 epitope of LFA-1 comprising incubating purified LFA-1 or a cell that expresses LFA-1 with a first test molecule and a second labeled molecule that specifically binds the R7.1 epitope of LFA-1 or binds LFA-1 such that the R7.1 epitope is modified; and detecting the second labeled molecule; wherein a decrease in binding of the second molecule indicates binding of the first test molecule.

The invention further provides methods for identifying a molecule that binds or modifies the R7.1 epitope of LFA-1 comprising incubating purified LFA-1 or a cell that expresses LFA-1 with (i) a first test molecule, (ii) a second molecule that specifically binds the R7.1 epitope of LFA-1 or binds LFA-1 such that the R7.1 epitope is modified, and (iii) a third labeled molecule, wherein the third labeled molecule binds the second molecule; and detecting the third labeled molecule bound to the second molecule; wherein a decrease in binding of the second molecule indicates binding of the first test molecule.

Another aspect of the invention provides methods for determining LFA-1 receptor occupancy comprising administering a first test molecule to a subject; withdrawing a sample of blood from the subject; incubating the sample with a second labeled molecule that specifically binds the R7.1 epitope of LFA-1 or binds LFA-1 such that the R7.1 epitope is modified; and detecting the amount of the second labeled molecule, wherein a decrease in the amount of binding of the second labeled molecule indicates binding of the first test molecule.

The invention further provides methods for determining LFA-1 receptor occupancy comprising administering a first test molecule to a subject; withdrawing a sample of blood from the subject; incubating the sample with a second molecule that specifically binds the R7.1 epitope of LFA-1 or binds LFA-1 such that the R7.1 epitope is modified and a third labeled molecule that binds the second molecule; and detecting the amount of the second molecule, wherein a decrease in the amount of binding of the second molecule indicates binding of the first test molecule.

In a specific embodiment, the molecule that specifically binds or modifies the R7.1 epitope of LFA-1 is a monoclonal antibody or fragment thereof. In another embodiment, the molecule that specifically binds or modifies the R7.1 epitope of LFA-1 is R7.1 (Bender MedSystems Diagnostics GmBH; Vienna, Austria). The invention further relates to equivalents of R7.1 (for example, molecules that bind or modify the R7.1 epitope of LFA-1) including but not limited to small molecules as described in: U.S. Pat. No. 6,355,664 by Kelly et al., issued Mar. 12, 2002; U.S. Pat. No. 6,492,408 by Kelly et al., issued Dec. 10, 2002; U.S. Pat. No. 6,414,153 by Kelly et al., issued Jul. 2, 2002, which are incorporated herein in their entireties. In another embodiment, the molecule that specifically binds or modifies the R7.1 epitope of LFA-1 is labeled with a fluorescent compound.

DETAILED DESCRIPTION OF THE INVENTION

Figure 1:
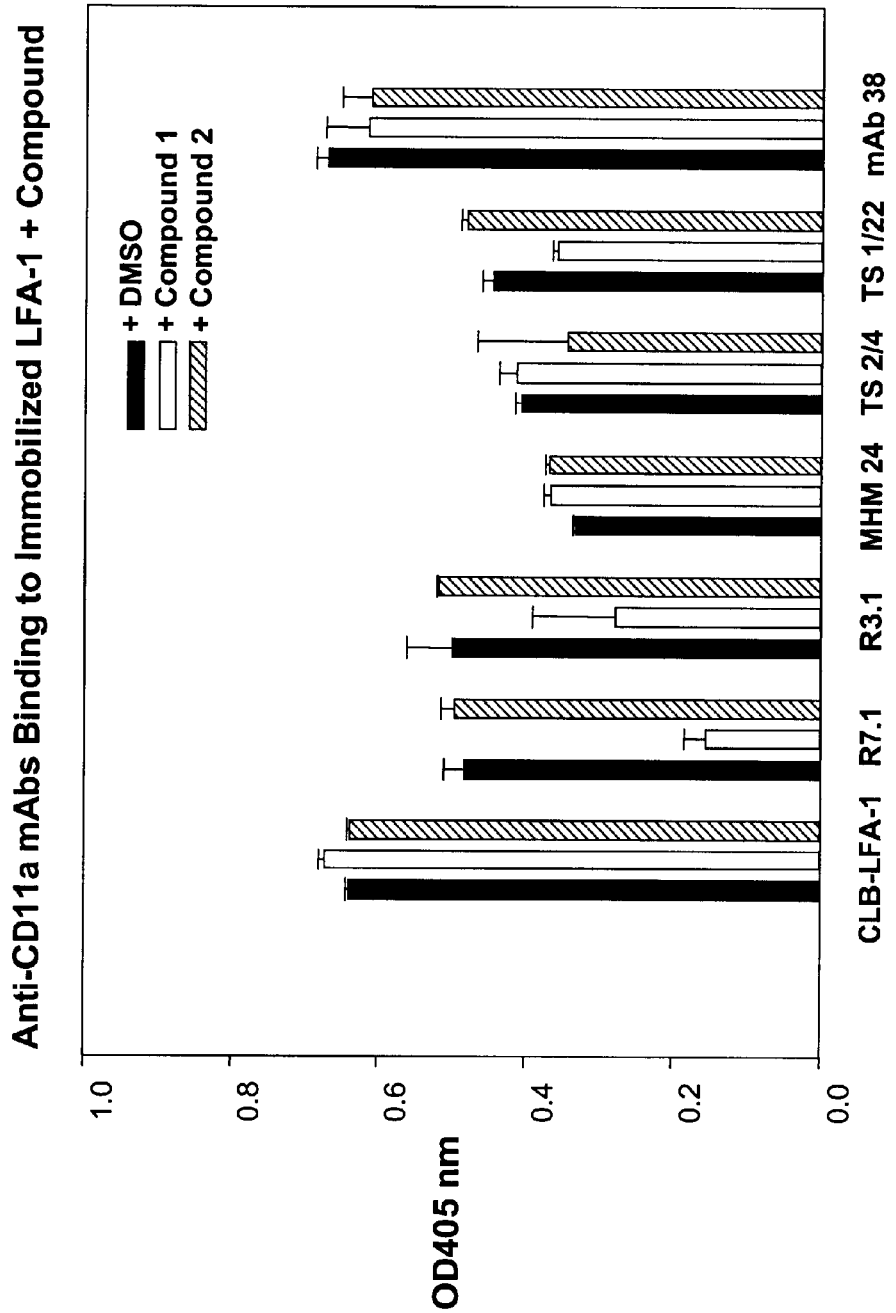
FIG. 1. Inhibition of monoclonal antibody (mAb) binding to Immobilized LFA-1 by Compound 1 (5 $\mu$M)((R)-5-(4-bromobenzyl)-3-(3,5-dichlorophenyl)-1,5-dimethylimidazolidine-2,4-dione). Immobilized LFA-1 was incubated with various anti-LFA-1 mAbs (CLB-LFA-1, R7.1, R3.1, MHM 24, TS 2/4, T/S 1/22, and mAb38) in the presence of Compound 1 (5 $\mu$M) or its enantiomer, Compound 2 (5 $\mu$M), or a dimethyl sulfoxide (DMSO) control. Absorbance at 405 nm is shown. Results are the mean of duplicate wells±SE.

The present invention provides useful screening methods and compositions for identifying molecules that specifically bind or modify the R7.1 epitope of LFA-1. The molecules thus identified may be useful therapeutic agents for treating or preventing inflammatory and immune cell mediated diseases. Another aspect of the invention relates to methods and molecules for determining LFA-1 receptor occupancy on target cells of a subject treated with a molecule that specifically binds or modifies the R7.1 epitope of LFA-1. The methods for determining receptor occupancy described herein can provide invaluable information in the clinic for determining, inter alia: how much compound has reached target cells after treatment; the amount of compound necessary to saturate LFA-1 receptors; and how much receptor occupancy is needed for efficacy. A third aspect provides molecules useful in the methods of the invention.

The invention provides methods for identifying a molecule that binds or modifies the R7.1 epitope of LFA-1 comprising incubating purified LFA-1 or a cell that expresses LFA-1 with a first test molecule and a second labeled molecule that specifically binds the R7.1 epitope of LFA-1 or binds LFA-1 such that the R7.1 epitope is modified; and detecting the second labeled molecule; wherein a decrease in binding of the second molecule indicates binding of the first test molecule.

The invention further provides methods for identifying a molecule that binds or modifies the R7.1 epitope of LFA-1 comprising incubating purified LFA-1 or a cell that expresses LFA-1 with (i) a first test molecule, (ii) a second molecule that specifically binds the R7.1 epitope of LFA-1 or binds LFA-1 such that the R7.1 epitope is modified, and (iii) a third labeled molecule, wherein the third labeled molecule binds the second molecule; and detecting the third labeled molecule bound to the second molecule; wherein a decrease in binding of the second molecule to the R7.1 epitope indicates binding of the first test molecule.

Another aspect of the invention provides methods for determining LFA-1 receptor occupancy comprising administering a first test molecule to a subject; withdrawing a sample of blood from the subject; incubating the sample with a second labeled molecule that specifically binds the R7.1 epitope of LFA-1 or binds LFA-1 such that the R7.1 epitope is modified; and detecting the amount of the second labeled molecule, wherein a decrease in the amount of binding of the second labeled molecule indicates binding of the first test molecule.

The invention further provides methods for determining LFA-1 receptor occupancy comprising administering a first test molecule to a subject; withdrawing a sample of blood from the subject; incubating the sample with a second molecule that specifically binds the R7.1 epitope of LFA-1 or binds LFA-1 such that the R7.1 epitope is modified and a third labeled molecule that binds the second molecule; and detecting the amount of the second molecule, wherein a decrease in the amount of binding of the second molecule indicates binding of the first test molecule.

The molecules of the invention that specifically bind or modify the R7.1 epitope of LFA-1 include but are not limited to: antibodies, preferably monoclonal antibodies (for example, R3.1 (Ma et al., 1992, Circulation 86:937), R7.1 (Bender MedSystems Diagnostics GmBH; Vienna, Austria)), derivatives or fragments thereof (for example, Fab fragments, F(ab')$_2$ fragments, fragments produced by a Fab expression library) and epitope-binding fragments of any of the above. In a specific embodiment, the molecule that specifically binds or modifies the R7.1 epitope of LFA-1 is mAb R7.1. In another embodiment, the molecule that specifically binds or modifies the R7.1 epitope of LFA-1 is a Fab fragment.

For preparation of monoclonal antibodies that specifically bind or modify the R7.1 epitope of LFA-1, any technique which provides for the production of antibody molecules by continuous cell lines in culture may be used. For example, the hybridoma technique originally developed by Köhler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985 in "Monoclonal Antibodies and Cancer Therapy", Alan R. Liss, Inc., pp. 77–96).

Antibody fragments that recognize the R7.1 epitope may be generated by known techniques. For example, such fragments include but are not limited to: the F(ab')$_2$ fragments which can be produced by pepsin digestion of the antibody molecule and the Fab fragments, which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity.

The molecules of the invention that specifically bind or modify the R7.1 epitope of LFA-1 may also include chemical compounds, including but not limited to small molecules such as those described in: U.S. Pat. No. 6,355,664 by Kelly et al., issued Mar. 12, 2002; U.S. Pat. No. 6,492,408 by Kelly et al., issued Dec. 10, 2002; U.S. Pat. No. 6,414,153 by Kelly et al., issued Jul. 2, 2002. Such compounds include but are not limited to those compounds of the formula I, formula II, and formula III shown below:

(I)

wherein:

Y is an oxygen or sulfur atom;

Z is an oxygen or sulfur atom;

X is a divalent group of the formula >CHR$^1$, >NR$^1$, >CHSO$_2$R$^1$, or >NSO$_2$R$^1$, or an oxygen or sulfur atom, wherein R$^1$ is:

(A) a hydrogen atom, (B) branched or unbranched alkyl of 1 to 6 carbon atoms or cycloalkyl of 3 to 6 carbon atoms, which alkyl or cycloalkyl group is optionally mono- or polysubstituted with:

(i) halogen, (ii) oxo, (iii) aryl, which is selected from the group consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl, wherein one or more hydrogen atoms of said aryl group is optionally and independently replaced with:

(a) alkyl of 1 to 3 carbon atoms, (b) —COOH, (c) —SO$_2$OH, (d) —PO(OH)$_2$, (e) a group of the formula —COOR$^7$, wherein R$^7$ is straight or branched alkyl of 1 to 5 carbon atoms or cycloalkyl of 3 to 5 carbon atoms, (f) a group of the formula —NR$^8$R$^9$, wherein R$^8$ and R$^9$ are each independently a hydrogen atom, alkyl of 1 to 6 carbon atoms, cycloalkyl of 3 to 6 carbon atoms or acyl of 1 to 7 carbon atoms, or wherein R$^8$ and R$^9$ constitute a saturated hydrocarbon bridge of 3 to 5 carbon atoms which together with the nitrogen atom between them form a heterocyclic ring, (g) a group of the formula $-CONR^{10}R^{11}$, wherein $R^{10}$ and $R^{11}$ are each independently a hydrogen atom, alkyl of 1 to 6 carbon atoms or cycloalkyl of 3 to 6 carbon atoms, or wherein $R^{10}$ and $R^{11}$ constitute a saturated hydrocarbon bridge of 3 to 5 carbon atoms which together with the nitrogen atom between them form a heterocyclic ring, (h) a group of the formula $-OR^{12a}$, wherein $R^{12a}$ is a hydrogen atom, or an alkyl or acyl group of 1 to 7 carbon atoms, (i) a group of the formula $-SR^{12b}$, wherein $R^{12b}$ is a hydrogen atom, or an alkyl or acyl group of 1 to 7 carbon atoms, (j) cyano, or (k) an amidino group of the formula:

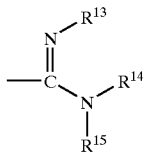

wherein $R^{13}$, $R^{14}$ and $R^{15}$ are each, independently, a hydrogen atom or alkyl of 1 to 3 carbon atoms, or wherein one of $R^{13}$, $R^{14}$ and $R^{15}$ is a hydrogen atom or alkyl of 1 to 3 carbon atoms and wherein the remaining two of $R^{13}$, $R^{14}$ and $R^{15}$ together form a saturated hydrocarbon bridge of 3 to 5 carbon atoms which together with the nitrogen atom(s) between them form a heterocyclic ring, (iv) a group of the formula $-COOR^{16}$, wherein $R^{16}$ is straight or branched alkyl of 1 to 7 carbon atoms or cycloalkyl of 3 to 6 carbon atoms, (v) cyano, (vi) a group of the formula $-CONR^{17}R^{18}$, wherein $R^{17}$ and $R^{18}$ are each, independently, a hydrogen atom, alkyl of 1 to 6 carbon atoms or cycloalkyl of 3 to 6 carbon atoms, or wherein $R^{17}$ and $R^{18}$ constitute a saturated hydrocarbon bridge of 3 to 5 carbon atoms which together with the nitrogen atom between them form a heterocyclic ring, (vii) a group of the formula $-OR^{19}$, wherein $R^{19}$ is a hydrogen atom, or an alkyl or acyl group of 1 to 7 carbon atoms, (viii) a group of the formula $-SR^{20}$, wherein $R^{20}$ is a hydrogen atom, or an alkyl or acyl group of 1 to 7 carbon atoms, (ix) a group of the formula $-NR^{21}R^{22}$, wherein $R^{21}$ and $R^{22}$ are each, independently,
(a) a hydrogen atom,
(b) alkyl or acyl of 1 to 7 carbon atoms or cycloalkyl of 3 to 7 carbon atoms,
(c) a group of the formula $-(CH_2)_mCOOH$, wherein m is 0, 1 or 2, or
(d) a group of the formula $-(CH_2)_nCOOR^{23}$, wherein n is 0, 1 or 2, wherein $R^{23}$ is straight or branched alkyl of 1 to 6 carbon atoms, or wherein $R^{21}$ and $R^{22}$ constitute a saturated hydrocarbon bridge of 3 to 5 carbon atoms which together with the nitrogen atom between them form a heterocyclic ring, or (x) a quaternary group of the formula:

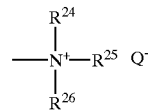

wherein $R^{24}$, $R^{25}$ and $R^{26}$ are each, independently, a branched or unbranched alkyl group of 1 to 7 carbon atoms and $Q^-$ is a chlorine, bromine or iodine counterion, (C) a branched or unbranched carboxylic acid group of 3 to 6 carbon atoms, (D) a branched or unbranched phosphonic acid group of 2 to 6 carbon atoms, (E) a branched or unbranched sulfonic acid group of 2 to 6 carbon atoms, (F) an amidino group of the formula:

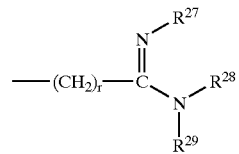

wherein r is 2, 3, 4, 5 or 6, and
$R^{27}$, $R^{28}$ and $R^{29}$ are each, independently, a hydrogen atom or alkyl of 1 to 3 carbon atoms, or wherein one of $R^{27}$, $R^{28}$ and $R^{29}$ is a hydrogen atom or alkyl of 1 to 3 carbon atoms and wherein the remaining two of $R^{27}$, $R^{28}$ and $R^{29}$ together form a saturated hydrocarbon bridge of 3 to 5 carbon atoms which together with the nitrogen atom(s) between them form a heterocyclic ring, (G) an guanidino group of the formula:

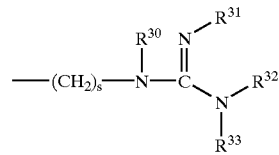

wherein s is 2, 3, 4, 5 or 6, and
$R^{30}$, $R^{31}$, $R^{32}$ and $R^{33}$ are each, independently, a hydrogen atom or alkyl of 1 to 3 carbon atoms, or wherein two of $R^{30}$, $R^{31}$, $R^{32}$ and $R^{33}$ are each, independently, a hydrogen atom or alkyl of 1 to 3 carbon atoms and wherein the remaining two of $R^{30}$, $R^{31}$, $R^{32}$ and $R^{33}$ together form a saturated hydrocarbon bridge of 3 to 5 carbon atoms which together with the nitrogen atom(s) between them form a heterocyclic ring, (H) piperidyl, wherein the nitrogen atom of said group is optionally substituted with:
(i) alkyl of 1 to 3 carbon atoms,
(ii) a carboxylic ester group of 2 to 7 carbon atoms,
(iii) a carboxylic acid group of 2 to 5 carbon atoms,
(iv) a phosphonic acid group of 1 to 6 carbon atoms, or
(v) a sulfonic acid groups of 1 to 6 carbon atoms, or (I) aryl which is selected from the group consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl, wherein one or more hydrogen atoms of said aryl group optionally and independently replaced with:
(i) alkyl of 1 to 3 carbon atoms,
(ii) —COOH,
(iii) —SO$_2$OH,
(iv) —PO(OH)$_2$,
(v) a group of the formula —COOR$^7$, wherein R$^7$ is straight or branched alkyl of 1 to 5 carbon atoms or cycloalkyl of 3 to 5 carbon atoms,
(vi) a group of the formula —NR$^8$R$^9$, wherein R$^8$ and R$^9$ are each, independently, a hydrogen atom, alkyl of 1 to 6 carbon atoms, cycloalkyl of 3 to 6 carbon atoms or acyl of 1 to 7 carbon atoms, or wherein R$^8$ and R$^9$ constitute a saturated hydrocarbon bridge of 3 to 5 carbon atoms which together with the nitrogen atom between them form a heterocyclic ring,
(vii) a group of the formula —CONR$^{10}$R$^{11}$, wherein R$^{10}$ and R$^{11}$ are each, independently, a hydrogen atom, alkyl of 1 to 6 carbon atoms or cycloalkyl of 3 to 6 carbon atoms, or wherein R$^{10}$ and R$^{11}$ constitute a saturated hydrocarbon bridge of 3 to 5 carbon atoms which together with the nitrogen atom between them form a heterocyclic ring,
(viii) a group of the formula —OR$^{12a}$, wherein R$^{12a}$ is a hydrogen atom, or an alkyl or acyl group of 1 to 7 carbon atoms,
(ix) a group of the formula —SR$^{12b}$, wherein R$^{12b}$ is a hydrogen atom, or an alkyl or acyl group of 1 to 7 carbon atoms,
(x) cyano, or
(xi) an amidino group of the formula:

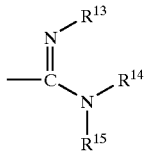

wherein R$^{13}$, R$^{14}$ and R$^{15}$ are each, independently, a hydrogen atom or alkyl of 1 to 3 carbon atoms, or wherein one of R$^{13}$, R$^{14}$ and R$^{15}$ is a hydrogen atom or alkyl of 1 to 3 carbon atoms and wherein the remaining two of R$^{13}$, R$^{14}$ and R$^{15}$ together form a saturated hydrocarbon bridge of 3 to 5 carbon atoms which together with the nitrogen atom(s) between them form a heterocyclic ring;

R$^2$ is:
(A) a hydrogen atom, or
(B) branched or unbranched alkyl of 1 to 3 carbon atoms or cycloalkyl of 3 to 5 carbon atoms wherein said alkyl or cycloalkyl group is optionally substituted with:
(i) a group of the formula —OR$^{34}$, wherein R$^{34}$ is a hydrogen atom, or an alkyl or acyl group of 1 to 7 carbon atoms, or
(ii) a group of the formula —NR$^{35}$R$^{36}$, wherein R$^{35}$ and R$^{36}$ are each, independently, a hydrogen atom, alkyl of 1 to 2 carbon atoms, or acyl of 1 to 2 carbon atoms;

R$^3$ is a group of the formula —(CR$^{37}$R$^{38}$)$_x$(CR$^{39}$R$^{40}$)$_y$R$^{41}$, wherein; x and y are each independently 0 or 1, R$^{37}$, R$^{38}$ and R$^{39}$ are each, independently:
(A) a hydrogen atom,
(B) a group of the formula —OR$^{42}$, wherein R$^{42}$ is a hydrogen atom, or an alkyl or acyl group of 1 to 7 carbon atoms, or
(C) branched or unbranched alkyl of 1 to 3 carbon atoms or cycloalkyl of 3 to 5 carbon atoms, R$^{40}$ is:
(A) a hydrogen atom,
(B) a group of the formula —OR$^{42}$, wherein R$^{42}$ is a hydrogen atom, or an alkyl or acyl group of 1 to 7 carbon atoms,
(C) branched or unbranched alkyl of 1 to 3 carbon atoms or cycloalkyl of 3 to 5 carbon atoms, or
(D) aryl which is selected from the group consisting of phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, -3, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-pthalaninyl, 2-, 3-, 6- or 7-quinoxalinyl, 2-, 3-, 6- or 7-napthyridinyl, 2-, 6- or 7-pteridinyl and 2-, 6- or 7-quinazolinyl, wherein one or more of the hydrogen atoms of said aryl group is optionally and independently replaced with:
(i) R$^{43}$, which is aryl selected from the group consisting of phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, -3, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-pthalaninyl, 2-, 3-, 6- or 7-quinoxalinyl, 2-, 3-, 6- or 7-napthyridinyl, 2-, 6- or 7-pteridinyl and 2-, 6- or 7-quinazolinyl, wherein one or more of the hydrogen atoms of said aryl group is optionally and independently replaced with:
(a) branched or unbranched alkyl of 1 to 6 carbon atoms or cycloalkyl of 3 to 6 carbon atoms, which alkyl or cycloalkyl group is mono- or polysubstituted with halogen or oxo,
(b) —COOH,
(c) —SO$_2$OH,
(d) —PO(OH)$_2$,
(e) a group of the formula —COOR$^{44}$, wherein R$^{44}$ is straight or branched alkyl of 1 to 5 carbon atoms or cycloalkyl of 3 to 5 carbon atoms,
(f) a group of the formula —NR$^{45}$R$^{46}$, wherein R$^{45}$ and R$^{46}$ are each, independently, a hydrogen atom, alkyl or fluoroalkyl of 1 to 6 carbon atoms, cycloalkyl of 3 to 6 carbon atoms or acyl of 1 to 7 carbon atoms, or wherein $R^{45}$ and $R^{46}$ constitute a saturated hydrocarbon bridge of 3 to 5 carbon atoms which together with the nitrogen atom between them form a heterocyclic ring, (g) a group of the formula —$CONR^{47}R^{48}$, wherein $R^{47}$ and $R^{48}$ are each independently a hydrogen atom, alkyl or fluoroalkyl of 1 to 6 carbon atoms or cycloalkyl of 3 to 6 carbon atoms, or wherein $R^{47}$ and $R^{48}$ constitute a saturated hydrocarbon bridge of 3 to 5 carbon atoms which together with the nitrogen atom between them form a heterocyclic ring, (h) a group of the formula —$OR^{49}$, wherein $R^{49}$ is a hydrogen atom, or an alkyl, fluoroalkyl or acyl group of 1 to 7 carbon atoms, (i) a group of the formula —$SR^{50}$, wherein $R^{50}$ is a hydrogen atom, or an alkyl, fluoroalkyl or acyl group of 1 to 7 carbon atoms, (j) cyano, (k) nitro, (l) an amidino group of the formula:

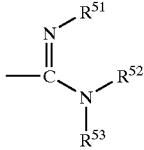

wherein $R^{51}$, $R^{52}$ and $R^{53}$ are each, independently, a hydrogen atom or alkyl of 1 to 3 carbon atoms, or wherein one of $R^{51}$, $R^{52}$ and $R^{53}$ is a hydrogen atom or alkyl of 1 to 3 carbon atoms and wherein the remaining two of $R^{51}$, $R^{52}$ and $R^{53}$ together form a saturated hydrocarbon bridge of 3 to 5 carbon atoms which together with the nitrogen atom(s) between them form a heterocyclic ring, or (m) halogen, (ii) methyl, which is optionally mono- or polysubstituted with fluorine atoms and additionally is optionally monosubstituted with $R^{43}$, (iii) branched or unbranched alkyl of 2 to 6 carbon atoms or cycloalkyl of 3 to 6 carbon atoms, which alkyl or cycloalkyl group is optionally mono- or polysubstituted with halogen or oxo, (iv) a group of the formula —$COOR^{54}$, wherein $R^{54}$ is straight or branched alkyl of 1 to 5 carbon atoms or cycloalkyl of 3 to 5 carbon atoms, (v) a group of the formula —$NR^{55}R^{56}$, wherein $R^{55}$ and $R^{56}$ are each, independently, a hydrogen atom, alkyl or fluoroalkyl of 1 to 6 carbon atoms, cycloalkyl of 3 to 6 carbon atoms or acyl of 1 to 7 carbon atoms, or wherein $R^{55}$ and $R^{56}$ constitute a saturated hydrocarbon bridge of 3 to 5 carbon atoms which together with the nitrogen atom between them form a heterocyclic ring, and wherein one of $R^{55}$ and $R^{56}$ additionally is optionally the group $R^{43}$, (vi) a group of the formula —$CONR^{57}R^{58}$, wherein $R^{57}$ and $R^{58}$ are each, independently, a hydrogen atom, alkyl or fluoroalkyl of 1 to 6 carbon atoms or cycloalkyl of 3 to 6 carbon atoms, or wherein $R^{57}$ and $R^{58}$ constitute a saturated hydrocarbon bridge of 3 to 5 carbon atoms which together with the nitrogen atom between them form a heterocyclic ring, and wherein one of $R^{57}$ and $R^{58}$ additionally is optionally the group $R^{43}$, (vii) a group of the formula —$COR^{59}$, wherein $R^{59}$ is a hydrogen atom, straight or branched alkyl of 1 to 5 carbon atoms, cycloalkyl of 3 to 5 carbon atoms or $R^{43}$ (viii) a group of the formula —$OR^{60}$, wherein $R^{60}$ is a hydrogen atom, an alkyl, fluoroalkyl or acyl group of 1 to 7 carbon atoms, or $R^{43}$, (ix) a group of the formula —$SR^{61}$, wherein $R^{61}$ is a hydrogen atom, an alkyl, fluoroalkyl or acyl group of 1 to 7 carbon atoms, or $R^{43}$, (x) cyano, (xi) nitro, or (xii) halogen, $R^{41}$ is:

aryl selected from the group consisting of phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, -3, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-pthalaninyl, 2-, 3-, 6- or 7-quinoxalinyl, 2-, 3-, 6- or 7-napthyridinyl, 2-, 6- or 7-pteridinyl and 2-, 6- or 7-quinazolinyl, wherein one or more of the hydrogen atoms of said aryl group is optionally and independently replaced with:

(A) $R^{62}$, which is aryl selected from the group consisting of phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, -3, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-pthalaninyl, 2-, 3-, 6- or 7-quinoxalinyl, 2-, 3-, 6- or 7-napthyridinyl, 2-, 6- or 7-pteridinyl and 2-, 6- or 7-quinazolinyl, wherein one or more of the hydrogen atoms of said aryl group is optionally and independently replaced with:

(i) branched or unbranched alkyl of 1 to 6 carbon atoms or cycloalkyl of 3 to 6 carbon atoms, which alkyl or cycloalkyl group is optionally mono- or polysubstituted with halogen or oxo, (ii) —COOH, (iii) —$SO_2OH$, (iv) —$PO(OH)_2$, (v) a group of the formula —$COOR^{63}$, wherein $R^{63}$ is straight or branched alkyl of 1 to 5 carbon atoms or cycloalkyl of 3 to 5 carbon atoms, (vi) a group of the formula —$NR^{64}R^{65}$, wherein $R^{64}$ and $R^{65}$ are each, independently, a hydrogen atom, alkyl or fluoroalkyl of 1 to 6 carbon atoms, cycloalkyl of 3 to 6 carbon atoms or acyl of 1 to 7 carbon atoms, or wherein $R^{64}$ and $R^{65}$ constitute a saturated hydrocarbon bridge of 3 to 5 carbon atoms which together with the nitrogen atom between them form a heterocyclic ring, (vii) a group of the formula —CONR$^{66}$R$^{67}$, wherein R$^{66}$ and R$^{67}$ are each, independently, a hydrogen atom, alkyl or fluoroalkyl of 1 to 6 carbon atoms or cycloalkyl of 3 to 6 carbon atoms, or wherein R$^{66}$ and R$^{67}$ constitute a saturated hydrocarbon bridge of 3 to 5 carbon atoms which together with the nitrogen atom between them form a heterocyclic ring, (viii) a group of the formula —OR$^{68}$, wherein R$^{68}$ is a hydrogen atom, or an alkyl, fluoroalkyl or acyl group of 1 to 7 carbon atoms, (ix) a group of the formula —SR$^{69}$, wherein R$^{69}$ is a hydrogen atom, or an alkyl, fluoroalkyl or acyl group of 1 to 7 carbon atoms, (x) cyano, (xi) nitro, or (xii) an amidino group of the formula:

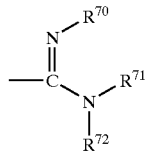

wherein $R^{70}$, $R^{71}$ and $R^{72}$ are each, independently, a hydrogen atom or alkyl or fluoroalkyl of 1 to 3 carbon atoms, or wherein one of $R^{70}$, $R^{71}$ and $R^{72}$ is a hydrogen atom or alkyl or fluoroalkyl of 1 to 3 carbon atoms and wherein the remaining two of $R^{70}$, $R^{71}$ and $R^{72}$ together form a saturated hydrocarbon bridge of 3 to 5 carbon atoms which together with the nitrogen atom(s) between them form a heterocyclic ring, or (xiii) halogen, (B) methyl, which is optionally mono- or polysubstituted with fluorine atoms and additionally is optionally monosubstituted with R$^{62}$, (C) branched or unbranched alkyl of 2 to 6 carbon atoms or cycloalkyl of 3 to 6 carbon atoms, which alkyl or cycloalkyl group is optionally mono- or polysubstituted with halogen or oxo, (D) a group of the formula —COOR$^{73}$, wherein R$^{73}$ is straight or branched alkyl of 1 to 5 carbon atoms or cycloalkyl of 3 to 5 carbon atoms, (E) a group of the formula —NR$^{74}$R$^{75}$, wherein R$^{74}$ and R$^{75}$ are each, independently, a hydrogen atom, alkyl or fluoroalkyl of 1 to 6 carbon atoms, cycloalkyl of 3 to 6 carbon atoms or acyl of 1 to 7 carbon atoms, or wherein R$^{74}$ and R$^{75}$ constitute a saturated hydrocarbon bridge of 3 to 5 carbon atoms which together with the nitrogen atom between them form a heterocyclic ring, and wherein one of R$^{74}$ and R$^{75}$ additionally is optionally the group R$^{62}$, (F) a group of the formula —CONR$^{76}$R$^{77}$, wherein R$^{76}$ and R$^{77}$ are each, independently, a hydrogen atom, alkyl or fluoroalkyl of 1 to 6 carbon atoms or cycloalkyl of 3 to 6 carbon atoms, or wherein R$^{76}$ and R$^{77}$ constitute a saturated hydrocarbon bridge of 3 to 5 carbon atoms which together with the nitrogen atom between them form a heterocyclic ring, and wherein one of R$^{76}$ and R$^{77}$ additionally is optionally the group R$^{62}$, (G) a group of the formula —COR$^{78}$, wherein R$^{78}$ is a hydrogen atom, straight or branched alkyl of 1 to 5 carbon atoms, cycloalkyl of 3 to 5 carbon atoms or R$^{62}$, (H) a group of the formula —OR$^{79}$, wherein R$^{79}$ is a hydrogen atom, an alkyl, fluoroalkyl or acyl group of 1 to 7 carbon atoms, or R$^{62}$, (I) a group of the formula —SR$^{80}$, wherein R$^{80}$ is a hydrogen atom, an alkyl, fluoroalkyl or acyl group of 1 to 7 carbon atoms, or R$^{62}$, (J) cyano, (K) nitro, or (L) halogen;

$R^4$ is Cl or trifluoromethyl; and, $R^5$ and $R^6$ are each, independently, a hydrogen, fluorine, chlorine, bromine or iodine atom, methyl or trifluoromethyl;

or a pharmaceutically acceptable salt thereof;

(II)

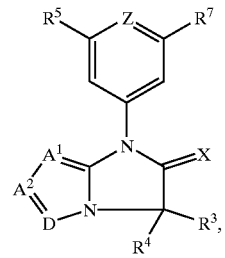

wherein:

$A^1$ is =N— or =C(H)—;

$A^2$ is =N—, =C(H)—, or =C(R')— wherein R' is halogen, —CN, -Oalkyl, —CO$_2$alkyl or —SO$_2$alkyl, wherein the foregoing alkyl moieties are of 1 to 3 carbon atoms;

D is =N—, =C(R$^1$)—, =C(H)—, =C(SO$_2$R$^1$)—, =C(S(O)R$^1$)—, =C(C(O)R$^1$)—, =C(C(O)H)—, =C(SR$^{1a}$)—, =C(OR$^{1a}$)— or =C(NHR$^{1a}$)—, wherein R$^1$ is selected from the group consisting of:

(A) —R$^{100}$, which is:

branched or unbranched alkyl of 1 to 6 carbon atoms, alkenyl of 2 to 6 carbon atoms or cycloalkyl or cycloalkenyl of 3 to 6 carbon atoms, in which alkyl, alkenyl, cycloalkyl or cycloalkenyl group one or more hydrogen atoms are optionally and independently replaced with:

(i) halogen, (ii) oxo, (iii) aryl or heteroaryl which is selected from the group consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl, wherein one or more hydrogen atoms of said aryl or heteroaryl group are optionally and independently replaced with:

(a) alkyl of 1 to 3 carbon atoms, (b) —COOH, (c) —SO$_2$OH, (d) —PO(OH)$_2$, (e) a group of the formula —COOR$^8$, wherein R$^8$ is straight or branched alkyl of 1 to 5 carbon atoms or cycloalkyl of 3 to 5 carbon atoms, (f) a group of the formula —NR$^9$R$^{10}$, wherein R$^9$ and R$^{10}$ are each independently a hydrogen atom, alkyl of 1 to 6 carbon atoms, cycloalkyl of 3 to 6 carbon atoms or acyl of 1 to 7 carbon atoms, or wherein R$^9$ and R$^{10}$ constitute a saturated hydrocarbon bridge of 3 to 5 carbon atoms which together with the nitrogen atom between them form a heterocyclic ring, (g) a group of the formula —CONR$^{11}$R$^{12}$, wherein R$^{11}$ and R$^{12}$ are each independently a hydrogen atom, alkyl of 1 to 6 carbon atoms or cycloalkyl of 3 to 6 carbon atoms, or wherein R$^{11}$ and R$^{12}$ constitute a saturated hydrocarbon bridge of 3 to 5 carbon atoms which together with the nitrogen atom between them form a heterocyclic ring, and wherein one carbon atom in said hydrocarbon bridge is optionally replaced by —O—, —S—, S(O)—, SO$_2$—, —NH—, or —NMe—, (h) a group of the formula —OR$^{13}$, wherein R$^{13}$ is a hydrogen atom, or an alkyl or acyl group of 1 to 7 carbon atoms, (i) a group of the formula —SR$^{14}$, wherein R$^{14}$ is a hydrogen atom, or an alkyl or acyl group of 1 to 7 carbon atoms, (j) —CN, or (k) an amidino group of the formula:

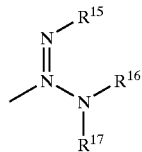

wherein R$^{15}$, R$^{16}$ and R$^{17}$ are each, independently, a hydrogen atom or alkyl of 1 to 3 carbon atoms, or wherein one of R$^{15}$, R$^{16}$ and R$^{17}$ is a hydrogen atom or alkyl of 1 to 3 carbon atoms and wherein the remaining two of R$^{15}$, R$^{16}$ and R$^{17}$ together form a saturated hydrocarbon bridge of 3 to 5 carbon atoms which together with the nitrogen atom(s) between them form a heterocyclic ring, (l) halogen, (m) a group of the formula —NHCONHalkyl, wherein the alkyl moiety contains 1 to 3 carbon atoms, (n) a group of the formula —NHCOOalkyl, wherein the alkyl moiety contains 1 to 3 carbon atoms, (iv) a group of the formula —COOR$^{18}$, wherein R$^{18}$ is straight or branched alkyl of 1 to 7 carbon atoms or cycloalkyl of 3 to 6 carbon atoms, (v) —CN, (vi) a group of the formula —CONR$^{19}$R$^{20}$, wherein R$^{19}$ and R$^{20}$ are each, independently, a hydrogen atom, alkyl of 1 to 6 carbon atoms or cycloalkyl of 3 to 6 carbon atoms, or wherein R$^{19}$ and R$^{20}$ constitute a saturated hydrocarbon bridge of 3 to 5 carbon atoms which together with the nitrogen atom between them form a heterocyclic ring, and wherein one carbon atom in said hydrocarbon bridge is optionally replaced by —O—, —S—, S(O)—, SO$_2$—, —NH—, or —NMe—, (vii) a group of the formula —OR$^{21}$, wherein R$^{21}$ is a hydrogen atom, or a straight or branched alkyl or acyl group of 1 to 7 carbon atoms, wherein one or more hydrogen atoms of said alkyl or acyl group are optionally replaced with a group independently selected from the group consisting of —OH, -Oalkyl (wherein the alkyl moiety contains 1 to 6 carbon atoms), —NH$_2$, —NHMe and —NMe$_2$, (viii) a group of the formula —SR$^{22}$, wherein R$^{22}$ is a hydrogen atom, or an alkyl or acyl group of 1 to 7 carbon atoms, wherein one or more hydrogen atoms of said alkyl or acyl group are optionally replaced with a group independently selected from the group consisting of —OH, -Oalkyl (wherein the alkyl moiety is 1 to 6 carbon atoms), —NH$_2$, —NHMe and —NMe$_2$, (ix) a group of the formula —NR$^{23}$R$^{24}$, wherein R$^{23}$ and R$^{24}$ are each, independently, (a) a hydrogen atom, (b) straight or branched alkyl or acyl of 1 to 7 carbon atoms or cycloalkyl of 3 to 7 carbon atoms, wherein said one or more hydrogen atoms of said alkyl or acyl group are optionally replaced with a group independently selected from the group consisting of —OH, -Oalkyl (wherein the alkyl moiety is 1 to 6 carbon atoms), —NH$_2$, —NHMe and —NMe$_2$, (c) a group of the formula —(CH$_2$)$_m$COOH, wherein m is 0, 1 or 2, (d) a group of the formula —(CH$_2$)$_n$COOR$^{25}$, wherein n is 0, 1 or 2, and wherein R$^{25}$ is straight or branched alkyl of 1 to 6 carbon atoms, or (e) a group of the formula —(CH$_2$)$_n$CONHR$^{25}$, wherein n is 0, 1 or 2, and wherein R$^{25}$ is straight or branched alkyl of 1 to 6 carbon atoms, (x) a quaternary group of the formula:

$$\begin{array}{c} R^{26} \\ | \\ -N^+-R^{27} \quad Q^- \\ | \\ R^{28} \end{array}$$

wherein R$^{26}$, R$^{27}$ and R$^{28}$ are each, independently, a branched or unbranched alkyl group of 1 to 7 carbon atoms and Q$^-$ is a pharmaceutically acceptable counter ion, (xi) a saturated, or partially unsaturated heterocyclic group selected from the group consisting of: imidazolinyl, imidazolidinyl, pyrrolinyl, pyrrolidinyl, piperidinyl, piperazinyl, morpholinyl, thiomorpholinyl, thiazolidinyl, azepinyl, tetrahydropyranyl, tetrahydrofuranyl, benzodioxolyl, tetrahydrothiophenyl and sulfolanyl, wherein said heterocyclic group is optionally mono- or polysubstituted with oxo, and (xii) a cycloalkyl group of 3 to 7 carbon atoms, (B) branched or unbranched carboxylic acid groups of 3 to 6 carbon atoms, (C) branched or unbranched phosphonic acid groups of 2 to 6 carbon atoms, (D) branched or unbranched sulfonic acid groups of 2 to 6 carbon atoms, (E) amidino groups of the formula:

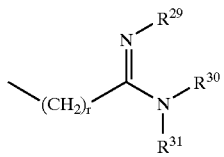

wherein r is 2, 3, 4, 5 or 6, and $R^{29}$, $R^{30}$ and $R^{31}$ are each, independently, a hydrogen atom or alkyl of 1 to 3 carbon atoms, or wherein one of $R^{29}$, $R^{30}$ and $R^{31}$ is a hydrogen atom or alkyl of 1 to 3 carbon atoms and wherein the remaining two of $R^{29}$, $R^{30}$ and $R^{31}$ together form a saturated hydrocarbon bridge of 3 to 5 carbon atoms which together with the nitrogen atom(s) between them form a heterocyclic ring, (F) guanidino groups of the formula:

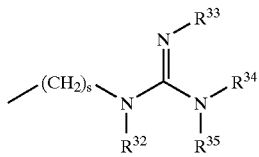

wherein s is 2, 3, 4, 5 or 6, and $R^{32}$, $R^{33}$, $R^{34}$ and $R^{35}$ are each, independently, a hydrogen atom or alkyl of 1 to 3 carbon atoms, or wherein two of $R^{32}$, $R^{33}$, $R^{34}$ and $R^{35}$ are each, independently a hydrogen atom or alkyl of 1 to 3 carbon atoms, and wherein the remaining two of $R^{32}$, $R^{33}$, $R^{34}$ and $R^{35}$ together form a saturated hydrocarbon bridge of 3 to 5 carbon atoms which together with the nitrogen atom(s) between them form a heterocyclic ring, (G) aryl or heteroaryl which is selected from the group consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl, wherein one or more hydrogen atoms of said aryl or heteroaryl group are optionally and independently replaced with:
(i) alkyl of 1 to 3 carbon atoms,
(ii) —COOH,
(iii) —SO$_2$OH,
(iv) —PO(OH)$_2$,
(v) a group of the formula —COOR$^{36}$, wherein R$^{36}$ is straight or branched alkyl of 1 to 5 carbon atoms or cycloalkyl of 3 to 5 carbon atoms,
(vi) a group of the formula —NR$^{37}$R$^{38}$, wherein R$^{37}$ and R$^{38}$ are each, independently, a hydrogen atom, alkyl of 1 to 6 carbon atoms, cycloalkyl of 3 to 6 carbon atoms or acyl of 1 to 7 carbon atoms, or wherein R$^{37}$ and R$^{38}$ constitute a saturated hydrocarbon bridge of 3 to 5 carbon atoms which together with the nitrogen atom between them form a heterocyclic ring,
(vii) a group of the formula —CONR$^{39}$R$^{40}$, wherein R$^{39}$ and R$^{40}$ are each, independently, a hydrogen atom, alkyl of 1 to 6 carbon atoms or cycloalkyl of 3 to 6 carbon atoms, or wherein R$^{39}$ and R$^{40}$ constitute a saturated hydrocarbon bridge of 3 to 5 carbon atoms which together with the nitrogen atom between them form a heterocyclic ring, and wherein one carbon atom in said hydrocarbon bridge is optionally replaced by —O—, —S—, S(O)—, SO$_2$—, —NH—, or —NMe—,
(viii) a group of the formula —OR$^{41}$, wherein R$^{41}$ is a hydrogen atom, or an alkyl or acyl group of 1 to 7 carbon atoms,
(ix) a group of the formula —SR$^{42}$, wherein R$^{42}$ is a hydrogen atom, or an alkyl or acyl group of 1 to 7 carbon atoms,
(x) —CN, or
(xi) an amidino group of the formula:

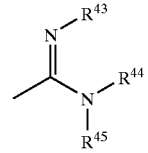

wherein R$^{43}$, R$^{44}$ and R$^{45}$ are each, independently, a hydrogen atom or alkyl of 1 to 3 carbon atoms, or wherein one of R$^{43}$, R$^{44}$ and R$^{45}$ is a hydrogen atom or alkyl of 1 to 3 carbon atoms and wherein the remaining two of R$^{43}$, R$^{44}$ and R$^{45}$ together form a saturated hydrocarbon bridge of 3 to 5 carbon atoms which together with the nitrogen atom(s) between them form a heterocyclic ring,
(H) groups of the formula —NR$^{46}$R$^{47}$, wherein R$^{46}$ and R$^{47}$ are each independently a hydrogen atom, phenyl which is optionally mono- or polysubstituted with halogen, or R$^{100}$, wherein R$^{100}$ is as hereinbefore defined,
(I) saturated or unsaturated heterocyclic groups or bicyclic heterocyclic groups selected from the group consisting of: imidazolinyl, imidazolidinyl, pyrrolinyl, pyrrolidinyl, piperidinyl, piperazinyl, morpholinyl, thiomorpholinyl, thiazolidinyl, azepinyl, tetrahydropyranyl, tetrahydrofuranyl, benzodioxolyl, tetrahydrothiophenyl and sulfolanyl, wherein said heterocyclic group is optionally mono- or poly-substituted with moieties selected from the group consisting of:
(i) oxo,
(ii) —OR$^{101}$, wherein R$^{101}$ is:
  (a) a hydrogen atom,
  (b) alkyl of 1 to 7 carbons, wherein any hydrogen atom of said alkyl group is optionally replaced with —OH, —OR$^{110}$ (wherein R$^{110}$ is an alkyl moiety of 1 to 6 carbon atoms), —NH$_2$, —NHMe or —NMe$_2$,
  (c) acyl of 1 to 7 carbons, wherein any hydrogen atom of said acyl group is optionally replaced with —OH, —OR$^{111}$ (wherein R$^{111}$ is an alkyl moiety of 1 to 6 carbon atoms), —NH$_2$, —NHMe or —NMe$_2$,
  (d) —CONR$^{102}$R$^{103}$, wherein R$^{102}$ and R$^{103}$ are each independently a hydrogen atom or alkyl of 1 to 7 atoms, or wherein R$^{102}$ and R$^{103}$ constitute a saturated hydrocarbon bridge of 3 to 5 carbon atoms which together with the nitrogen atom between them form a heterocyclic ring, and wherein one carbon atom in said hydrocarbon bridge is optionally replaced by —O—, —S—, S(O)—, SO$_2$—, —NH—, or —NMe—, or (e) —COOR$^{104}$, wherein R$^{104}$ is alkyl of 1 to 7 atoms,
(iii) —CONR$^{105}$R$^{106}$, wherein R$^{105}$ and R$^{106}$ are each independently:
  (a) a hydrogen atom,
  (b) straight or branched alkyl of 1 to 7 atoms or cycloalkyl of 3 to 7 atoms,
  (c) benzoyl,
  (d) benzyl or
  (e) phenyl, wherein said phenyl ring is optionally mono- or polysubstituted with —OR$^{112}$, wherein R$^{112}$ is alkyl of 1 to 6 carbon atoms,
or, wherein R$^{105}$ and R$^{106}$ constitute a saturated hydrocarbon bridge of 3 to 5 carbon atoms which together with the nitrogen atom between them form a heterocyclic ring, and wherein one carbon atom in said hydrocarbon bridge is optionally replaced by —O—, —S—, S(O)—, SO$_2$—, —NH—, or —NMe—,
(iv) —COOR$^{107}$, wherein R$^{107}$ is a hydrogen atom, or straight or branched alkyl of 1 to 7 carbon atoms,
(v) straight or branched alkyl of 1 to 7 carbon atoms, alkenyl or alkynyl of 2 to 7 carbon atoms, or cycloalkyl of 3 to 7 carbons, wherein one or more hydrogen atoms of said alkyl, alkenyl, alkynyl or cycloalkyl group is optionally replaced with a moiety independently selected from the group consisting of:
  (a) oxo,
  (b) —OH,
  (c) —OR$^{113}$, wherein R$^{113}$ is alkyl of 1 to 6 carbon atoms,
  (d) —OCOCH$_3$,
  (e) —NH$_2$,
  (f) —NHMe,
  (g) —NMe$_2$,
  (h) —CO$_2$H, and
  (i) —CO$_2$R$^{114}$ wherein R$^{114}$ is alkyl of 1 to 3 carbon atoms, or cycloalkyl of 3 to 7 carbons,
(vi) acyl of 1 to 7 carbon atoms, which is straight, branched or cyclic, and wherein one or more hydrogen atoms of said acyl group is optionally replaced with a moiety independently selected from the group consisting of:
  (a) —OH,
  (b) —OR$^{115}$, wherein R$^{115}$ is alkyl of 1 to 6 carbon atoms,
  (c) —NH$_2$,
  (d) —NHMe,
  (e) —NMe$_2$,
  (f) —NHCOMe,
  (g) oxo,
  (h) —CO$_2$R$^{116}$, wherein R$^{116}$ is alkyl of 1 to 3 carbon atoms,
  (i) —CN,
  (j) the halogen atoms,
  (k) heterocycles selected from the group consisting of imidazolinyl, imidazolidinyl, pyrrolinyl, pyrrolidinyl, piperidinyl, piperazinyl, morpholinyl, thiomorpholinyl, thiazolidinyl, azepinyl, tetrahydropyranyl, tetrahydrofuranyl, benzodioxolyl, tetrahydrothiophenyl and sulfolanyl, and
  (l) aryl or heteroaryl selected from the group consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl,
(vii) —SO$_2$R$^{108}$, wherein R$^{108}$ is:
  (a) aryl or heteroaryl which is selected from the group consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl, wherein said aryl or heteroaryl moiety is optionally substituted with one or more moieties selected from the group consisting of the halogen atoms, straight or branched alkyl of 1 to 6 carbons, and —OR$^{117}$ (wherein R$^{117}$ is hydrogen or alkyl of 1 to 6 carbon atoms),
  (b) a heterocyclic group selected from the group consisting of imidazolinyl, imidazolidinyl, pyrrolinyl, pyrrolidinyl, piperidinyl, piperazinyl, morpholinyl, thiomorpholinyl, thiazolidinyl, azepinyl, tetrahydropyranyl, tetrahydrofuranyl, benzodioxolyl, tetrahydrothiophenyl and sulfolanyl, wherein said heterocyclic group is optionally substituted with one or more moieties selected from the group consisting of the halogen atoms, straight or branched alkyl of 1 to 6 carbons, and —OR$^{118}$ (wherein R$^{118}$ is hydrogen or alkyl of 1 to 6 carbon atoms), or
  (c) straight or branched alkyl of 1 to 7 atoms, wherein said alkyl moiety is optionally substituted with one or more moieties selected from the group consisting of the halogen atoms, straight or branched alkyl of 1 to 6 carbons, and —OR$^{119}$ (wherein R$^{119}$ is hydrogen or alkyl of 1 to 6 carbon atoms),
(viii) —COR$^{109}$, wherein R$^{109}$ is:
  (a) aryl or heteroaryl which is selected from the group consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl, wherein said aryl or heteroaryl moiety is optionally substituted with one or more moieties selected from the group consisting of the halogen atoms, straight or branched alkyl of 1 to 6 carbons, and —OR$^{120}$ (wherein R$^{120}$ is hydrogen or alkyl of 1 to 6 carbon atoms),
  (b) a heterocyclic group selected from the group consisting of imidazolinyl, imidazolidinyl, pyrrolinyl, pyrrolidinyl, piperidinyl, piperazinyl, morpholinyl, thiomorpholinyl, thiazolidinyl, azepinyl, tetrahydropyranyl, tetrahydrofuranyl, benzodioxolyl, tetrahydrothiophenyl and sulfolanyl, wherein said heterocyclyl is optionally substituted with one or more halogen, straight or branched alkyl of 1 to 6 carbons, or —OR$^{121}$ (wherein R$^{121}$ is hydrogen or alkyl of 1 to 6 carbon atoms), or
  (c) straight or branched alkyl of 1 to 7 atoms, wherein said alkyl moiety is optionally substituted with one or more moieties selected from the group consisting of the halogen atoms, straight or branched alkyl of 1 to 6 carbons, and —OR$^{122}$ (wherein R$^{122}$ is hydrogen or alkyl of 1 to 6 carbon atoms),
(ix) —CHO,
(x) the halogen atoms, and
(xi) aryl or heteroaryl which is selected from the group consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl,
(J) the halogen atoms, and
(K) —CN, and
wherein R$^{1a}$ is R$^{100}$;
X is an oxygen or sulfur atom;
R$^3$ is:
  (A) a hydrogen atom, or
  (B) branched or unbranched alkyl of 1 to 3 carbon atoms or cycloalkyl of 3 to 5 carbon atoms wherein said alkyl or cycloalkyl group is optionally substituted with:
    (i) a group of the formula —OR$^{48}$, wherein R$^{48}$ is a hydrogen atom, or an alkyl or acyl group of 1 to 7 carbon atoms, or
    (ii) a group of the formula —NR$^{49}$R$^{50}$, wherein R$^{49}$ and R$^{50}$ are each, independently, a hydrogen atom, alkyl of 1 to 2 carbon atoms, or acyl of 1 to 2 carbon atoms;
R$^4$ is a group of the formula —(CR$^{51}$R$^{52}$)$_x$(CR$^{53}$R$^{54}$)$_y$R$^{55}$, wherein,
  x is 0 or 1,
  y is 0 or 1,
R$^{51}$, R$^{52}$ and R$^{53}$ are each, independently:
  (A) a hydrogen atom,
  (B) a group of the formula —OR$^{56}$, wherein R$^{56}$ is a hydrogen atom, or an alkyl or acyl group of 1 to 7 carbon atoms, or
  (C) branched or unbranched alkyl of 1 to 3 carbon atoms or cycloalkyl of 3 to 5 carbon atoms,
R$^{54}$ is:
  (A) a group of the formula R$^{57}$, wherein R$^{57}$ is independently selected from the same group as is R$^1$, or
  (B) a group of the formula —OR$^{58}$, wherein R$^{58}$ is independently selected from the same group as is R$^1$;
R$^{55}$ is:
aryl or heteroaryl which is selected from the group consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl, wherein one or more of the hydrogen atoms of said aryl or heteroaryl group is optionally and independently replaced with:
(A) R$^{59}$, which is aryl or heteroaryl selected from the group consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl, wherein one or more of the hydrogen atoms of said aryl or heteroaryl group is optionally and independently replaced with:
  (i) branched or unbranched alkyl of 1 to 6 carbon atoms or cycloalkyl of 3 to 6 carbon atoms, which alkyl or cycloalkyl group is optionally mono- or polysubstituted with halogen or oxo,
  (ii) a group of the formula —COOR$^{60}$, wherein R$^{60}$ is straight or branched alkyl of 1 to 5 carbon atoms or cycloalkyl of 3 to 5 carbon atoms,
  (iii) a group of the formula —NR$^{61}$R$^{62}$, wherein R$^{61}$ and R$^{62}$ are each, independently, a hydrogen atom, alkyl or fluoroalkyl of 1 to 6 carbon atoms, cycloalkyl of 3 to 6 carbon atoms or acyl of 1 to 7 carbon atoms, or wherein R$^{61}$ and R$^{62}$ constitute a saturated hydrocarbon bridge of 3 to 5 carbon atoms which together with the nitrogen atom between them form a heterocyclic ring,
  (iv) a group of the formula —CONR$^{63}$R$^{64}$, wherein R$^{63}$ and R$^{64}$ are each, independently, a hydrogen atom, alkyl or fluoroalkyl of 1 to 6 carbon atoms or cycloalkyl of 3 to 6 carbon atoms, or wherein R$^{63}$ and R$^{64}$ constitute a saturated hydrocarbon bridge of 3 to 5 carbon atoms which together with the nitrogen atom between them form a heterocyclic ring,
  (v) a group of the formula —OR$^{65}$, wherein R$^{65}$ is a hydrogen atom, or an alkyl, fluoroalkyl or acyl group of 1 to 7 carbon atoms,
  (vi) a group of the formula —SR$^{66}$, wherein R$^{66}$ is a hydrogen atom, or an alkyl, fluoroalkyl or acyl group of 1 to 7 carbon atoms,
  (vii) —CN,
  (viii) nitro, or
  (ix) halogen,
(B) methyl, which is optionally mono- or polysubstituted with fluorine atoms and additionally is optionally monosubstituted with R$^{59}$,
(C) branched or unbranched alkyl of 2 to 6 carbon atoms or cycloalkyl of 3 to 6 carbon atoms, which alkyl or cycloalkyl group is optionally mono- or polysubstituted with halogen or oxo,
(D) a group of the formula —COOR$^{67}$, wherein R$^{67}$ is straight or branched alkyl of 1 to 5 carbon atoms or cycloalkyl of 3 to 5 carbon atoms,
(E) a group of the formula —NR$^{68}$R$^{69}$, wherein R$^{68}$ and R$^{69}$ are each, independently, a hydrogen atom, alkyl or fluoroalkyl of 1 to 6 carbon atoms, cycloalkyl of 3 to 6 carbon atoms or acyl of 1 to 7 carbon atoms, or wherein R$^{68}$ and R$^{69}$ constitute a saturated hydrocarbon bridge of 3 to 5 carbon atoms which together with the nitrogen atom between them form a heterocyclic ring, and wherein one of R⁶⁸ and R⁶⁹ additionally is optionally the group R⁵⁹, (F) a group of the formula —CONR⁷⁰R⁷¹, wherein R⁷⁰ and R⁷¹ are each, independently, a hydrogen atom, alkyl or fluoroalkyl of 1 to 6 carbon atoms or cycloalkyl of 3 to 6 carbon atoms, or wherein R⁷⁰ and R⁷¹ constitute a saturated hydrocarbon bridge of 3 to 5 carbon atoms which together with the nitrogen atom between them form a heterocyclic ring, and wherein one of R⁷⁰ and R⁷¹ additionally is optionally the group R⁵⁹, (G) a group of the formula —COR⁷², wherein R⁷² is a hydrogen atom, straight or branched alkyl of 1 to 5 carbon atoms, cycloalkyl of 3 to 5 carbon atoms or (H) a group of the formula —OR⁷³, wherein R⁷³ is a hydrogen atom, an alkyl, fluoroalkyl or acyl group of 1 to 7 carbon atoms, or R⁵⁹

(I) a group of the formula —SR⁷⁴, wherein R⁷⁴ is a hydrogen atom, an alkyl, fluoroalkyl or acyl group of 1 to 7 carbon atoms, or R⁵⁹, (J) —CN, (K) nitro, or (L) halogen;

R⁵ is Cl or trifluoromethyl;

Z is =N— or =C(R⁶)— wherein R⁶ is a hydrogen, fluorine, chlorine, bromine or iodine atom, methyl or trifluoromethyl; and, R⁷ is a hydrogen, fluorine, chlorine, bromine or iodine atom, methyl, —CN, nitro or trifluoromethyl, with the condition that when Z is =N— or =C(H)—, R⁷ is chlorine, trifluoromethyl, —CN or nitro;

and pharmaceutically acceptable salts thereof;

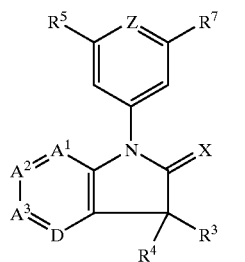

(III)

wherein:

A¹, A² and A³ are each, independently, N— or =CH—;

D is =N—, =CR¹—, =CSO₂R¹—, =CSOR¹—, =CSR¹—, =COR¹—, =CCOR¹—, or =CNHR¹—, wherein R¹ is:

(A) a hydrogen atom, (B) branched or unbranched alkyl of 1 to 6 carbon atoms or cycloalkyl of 3 to 6 carbon atoms, which alkyl or cycloalkyl group is optionally mono- or polysubstituted with:

(i) halogen, (ii) oxo, (iii) aryl which is selected from the group consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl, wherein one or more hydrogen atoms of said aryl group is optionally and independently replaced with:

(a) alkyl of 1 to 3 carbon atoms, (b) —COOH, (c) —SO₂OH, (d) —PO(OH)₂, (e) a group of the formula —COOR⁸, wherein R⁸ is straight or branched alkyl of 1 to 5 carbon atoms or cycloalkyl of 3 to 5 carbon atoms, (f) a group of the formula —NR⁹R¹⁰, wherein R⁹ and R¹⁰ are each independently a hydrogen atom, alkyl of 1 to 6 carbon atoms, cycloalkyl of 3 to 6 carbon atoms or acyl of 1 to 7 carbon atoms, or wherein R⁹ and R¹⁰ constitute a saturated hydrocarbon bridge of 3 to 5 carbon atoms which together with the nitrogen atom between them form a heterocyclic ring, (g) a group of the formula —CONR¹¹R¹², wherein R¹¹ and are each independently a hydrogen atom, alkyl of 1 to 6 carbon atoms or cycloalkyl of 3 to 6 carbon atoms, or wherein R¹¹ and R¹² constitute a saturated hydrocarbon bridge of 3 to 5 carbon atoms which together with the nitrogen atom between them form a heterocyclic ring, (h) a group of the formula —OR¹³, wherein R¹³ is a hydrogen atom, or an alkyl or acyl group of 1 to 7 carbon atoms, (i) a group of the formula —SR¹⁴, wherein R¹⁴ is a hydrogen atom, or an alkyl or acyl group of 1 to 7 carbon atoms, (j) cyano, or (k) an amidino group of the formula

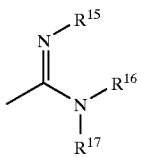

wherein R¹⁵, R¹⁶ and R¹⁷ are each, independently, a hydrogen atom or alkyl of 1 to 3 carbon atoms, or wherein one of R¹⁵, R¹⁶ and R¹⁷ is a hydrogen atom or alkyl of 1 to 3 carbon atoms and wherein the remaining two of R¹⁵, R¹⁶ and R¹⁷ together form a saturated hydrocarbon bridge of 3 to 5 carbon atoms which together with the nitrogen atom(s) between them form a heterocyclic ring, (iv) a group of the formula —COOR¹⁸, wherein R¹⁸ is straight or branched alkyl of 1 to 7 carbon atoms or cycloalkyl of 3 to 6 carbon atoms, (v) cyano, (vi) a group of the formula —CONR¹⁹R²⁰, wherein R¹⁹ and R²⁰ are each, independently, a hydrogen atom, alkyl of 1 to 6 carbon atoms or cycloalkyl of 3 to 6 carbon atoms, or wherein R¹⁹ and R²⁰ constitute a saturated hydrocarbon bridge of 3 to 5 carbon atoms which together with the nitrogen atom between them form a heterocyclic ring, (vii) a group of the formula —OR²¹, wherein R²¹ is a hydrogen atom, or an alkyl or acyl group of 1 to 7 carbon atoms, (viii) a group of the formula —SR²², wherein R²² is a hydrogen atom, or an alkyl or acyl group of 1 to 7 carbon atoms, (ix) a group of the formula —NR$^{23}$R$^{24}$, wherein R$^{23}$ and R$^{24}$ are each, independently,
  (a) a hydrogen atom,
  (b) alkyl or acyl of 1 to 7 carbon atoms or cycloalkyl of 3 to 7 carbon atoms,
  (c) a group of the formula —(CH$_2$)$_m$COOH, wherein m is 0, 1 or 2, or
  (d) a group of the formula —(CH$_2$)$_n$COOR$^{25}$, wherein n is 0, 1 or 2, wherein R$^{25}$ is straight or branched alkyl of 1 to 6 carbon atoms,
or wherein R$^{23}$ and R$^{24}$ constitute a saturated hydrocarbon bridge of 3 to 5 carbon atoms which together with the nitrogen atom between them form a heterocyclic ring, or
(x) a quaternary group of the formula:

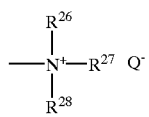

wherein R$^{26}$, R$^{27}$ and R$^{28}$ are each, independently, a branched or unbranched alkyl group of 1 to 7 carbon atoms and Q$^-$ is a chlorine, bromine or iodine counterion, (C) a branched or unbranched carboxylic acid group of 3 to 6 carbon atoms,
(D) a branched or unbranched phosphonic acid group of 2 to 6 carbon atoms,
(E) a branched or unbranched sulfonic acid group of 2 to 6 carbon atoms,
(F) an amidino group of the formula:

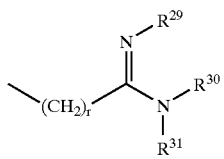

wherein r is 2, 3, 4, 5 or 6, and
R$^{29}$, R$^{30}$ and R$^{31}$ are each, independently, a hydrogen atom or alkyl of 1 to 3 carbon atoms, or wherein one of R$^{29}$, R$^{30}$ and R$^{31}$ is a hydrogen atom or alkyl of 1 to 3 carbon atoms and wherein the remaining two of R$^{29}$, R$^{30}$ and R$^{31}$ together form a saturated hydrocarbon bridge of 3 to 5 carbon atoms which together with the nitrogen atom(s) between them form a heterocyclic ring,
(G) an guanidino group of the formula:

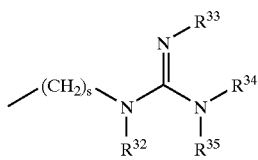

wherein s is 2, 3, 4, 5 or 6, and
R$^{32}$, R$^{33}$, R$^{34}$ and R$^{35}$ are each, independently, a hydrogen atom or alkyl of 1 to 3 carbon atoms, or wherein two of R$^{32}$, R$^{33}$, R$^{34}$ and R$^{35}$ are each, independently, a hydrogen atom or alkyl of 1 to 3 carbon atoms and wherein the remaining two of R$^{32}$, R$^{33}$, R$^{34}$ and R$^{35}$ together form a saturated hydrocarbon bridge of 3 to 5 carbon atoms which together with the nitrogen atom(s) between them form a heterocyclic ring,
(H) aryl which is selected from the group consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl, wherein one or more hydrogen atoms of said aryl group is optionally and independently replaced with:
  (i) alkyl of 1 to 3 carbon atoms,
  (ii) —COOH,
  (iii) —SO$_2$OH,
  (iv) —PO(OH)$_2$,
  (v) a group of the formula —COOR$^{36}$, wherein R$^{36}$ is straight or branched alkyl of 1 to 5 carbon atoms or cycloalkyl of 3 to 5 carbon atoms,
  (vi) a group of the formula —NR$^{37}$R$^{38}$, wherein R$^{37}$ and R$^{38}$ are each, independently, a hydrogen atom, alkyl of 1 to 6 carbon atoms, cycloalkyl of 3 to 6 carbon atoms or acyl of 1 to 7 carbon atoms, or wherein R$^{37}$ and R$^{38}$ constitute a saturated hydrocarbon bridge of 3 to 5 carbon atoms which together with the nitrogen atom between them form a heterocyclic ring,
  (vii) a group of the formula —CONR$^{39}$R$^{40}$, wherein R$^{39}$ and R$^{40}$ are each, independently, a hydrogen atom, alkyl of 1 to 6 carbon atoms or cycloalkyl of 3 to 6 carbon atoms, or wherein R$^{39}$ and R$^{40}$ constitute a saturated hydrocarbon bridge of 3 to 5 carbon atoms which together with the nitrogen atom between them form a heterocyclic ring,
  (viii) a group of the formula —OR$^{41}$, wherein R$^{41}$ is a hydrogen atom, or an alkyl or acyl group of 1 to 7 carbon atoms,
  (ix) a group of the formula —SR$^{42}$, wherein R$^{42}$ is a hydrogen atom, or an alkyl or acyl group of 1 to 7 carbon atoms,
  (x) cyano, or
  (xi) an amidino group of the formula:

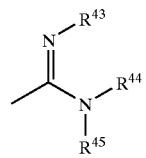

wherein R$^{43}$, R$^{44}$ and R$^{45}$ are each, independently, a hydrogen atom or alkyl of 1 to 3 carbon atoms, or wherein one of R$^{43}$, R$^{44}$ and R$^{45}$ is a hydrogen atom or alkyl of 1 to 3 carbon atoms and wherein the remaining two of R$^{43}$, R$^{44}$ and R$^{45}$ together form a saturated hydrocarbon bridge of 3 to 5 carbon atoms which together with the nitrogen atom(s) between them form a heterocyclic ring,
(I) a group of the formula —NR$^{46}$R$^{47}$, wherein R$^{46}$ and R$^{47}$ are each independently a hydrogen atom, alkyl of 1 to 6 carbon atoms, cycloalkyl of 3 to 6 carbon atoms or acyl of 1 to 7 carbon atoms, or wherein R$^{46}$ and R$^{47}$ constitute a saturated hydrocarbon bridge of 3 to 5 carbon atoms which together with the nitrogen atom between them form a heterocyclic ring, (J) a morpholinyl moiety, or, (K) halogen;

X is an oxygen or sulfur atom;

$R^3$ is:

(A) a hydrogen atom, or (B) branched or unbranched alkyl of 1 to 3 carbon atoms or cycloalkyl of 3 to 5 carbon atoms wherein said alkyl or cycloalkyl group is optionally substituted with:

(i) a group of the formula —$OR^{48}$, wherein $R^{48}$ is a hydrogen atom, or an alkyl or acyl group of 1 to 7 carbon atoms, or (ii) a group of the formula —$NR^{49}R^{50}$, wherein $R^{49}$ and $R^{50}$ are each, independently, a hydrogen atom, alkyl of 1 to 2 carbon atoms, or acyl of 1 to 2 carbon atoms;

$R^4$ is a group of the formula —$(CR^{51}R^{52})_x(CR^{53}R^{54})_yR^{55}$, wherein;

x and y are each independently 0 or 1, $R^{51}$, $R^{52}$ and $R^{53}$ are each, independently:

(A) a hydrogen atom, (B) a group of the formula —$OR^{56}$, wherein $R^{56}$ is a hydrogen atom, or an alkyl or acyl group of 1 to 7 carbon atoms, or (C) branched or unbranched alkyl of 1 to 3 carbon atoms or cycloalkyl of 3 to 5 carbon atoms, $R^{54}$ is:

(A) a group of the formula $R^{57}$, wherein $R^{57}$ is defined similarly to $R^1$ above, or (B) a group of the formula —$OR^{58}$, wherein $R^{58}$ is defined similarly to $R^1$ above;

$R^{55}$ is:

aryl selected from the group consisting of phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, -3, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-pthalaninyl, 2-, 3-, 6- or 7-quinoxalinyl, 2-, 3-, 6- or 7-napthyridinyl, 2-, 6- or 7-pteridinyl and 2-, 6- or 7-quinazolinyl, wherein one or more of the hydrogen atoms of said aryl group is optionally and independently replaced with:

(A) $R^{59}$, which is aryl selected from the group consisting of phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, -3, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-pthalaninyl, 2-, 3-, 6- or 7-quinoxalinyl, 2-, 3-, 6- or 7-napthyridinyl, 2-, 6- or 7-pteridinyl and 2-, 6- or 7-quinazolinyl, wherein one or more of the hydrogen atoms of said aryl group is optionally and independently replaced with:

(i) branched or unbranched alkyl of 1 to 6 carbon atoms or cycloalkyl of 3 to 6 carbon atoms, which alkyl or cycloalkyl group is optionally mono- or polysubstituted with halogen or oxo, (ii) a group of the formula —$COOR^{60}$, wherein $R^{60}$ is straight or branched alkyl of 1 to 5 carbon atoms or cycloalkyl of 3 to 5 carbon atoms, (iii) a group of the formula —$NR^{61}R^{62}$, wherein $R^{61}$ and $R^{62}$ are each, independently, a hydrogen atom, alkyl or fluoroalkyl of 1 to 6 carbon atoms, cycloalkyl of 3 to 6 carbon atoms or acyl of 1 to 7 carbon atoms, or wherein $R^{61}$ and $R^{62}$ constitute a saturated hydrocarbon bridge of 3 to 5 carbon atoms which together with the nitrogen atom between them form a heterocyclic ring, (iv) a group of the formula —$CONR^{63}R^{64}$, wherein $R^{63}$ and $R^{64}$ are each, independently, a hydrogen atom, alkyl or fluoroalkyl of 1 to 6 carbon atoms or cycloalkyl of 3 to 6 carbon atoms, or wherein $R^{63}$ and $R^{64}$ constitute a saturated hydrocarbon bridge of 3 to 5 carbon atoms which together with the nitrogen atom between them form a heterocyclic ring, (v) a group of the formula —$OR^{65}$, wherein $R^{65}$ is a hydrogen atom, or an alkyl, fluoroalkyl or acyl group of 1 to 7 carbon atoms, (vi) a group of the formula —$SR^{66}$, wherein $R^{66}$ is a hydrogen atom, or an alkyl, fluoroalkyl or acyl group of 1 to 7 carbon atoms, (vii) cyano, (viii) nitro, or (ix) halogen, (B) methyl, which is optionally mono- or polysubstituted with fluorine atoms and additionally is optionally monosubstituted with $R^{59}$, (C) branched or unbranched alkyl of 2 to 6 carbon atoms or cycloalkyl of 3 to 6 carbon atoms, which alkyl or cycloalkyl group is optionally mono- or polysubstituted with halogen or oxo, (D) a group of the formula —$COOR^{67}$, wherein $R^{67}$ is straight or branched alkyl of 1 to 5 carbon atoms or cycloalkyl of 3 to 5 carbon atoms, (E) a group of the formula —$NR^{68}R^{69}$, wherein $R^{68}$ and $R^{69}$ are each, independently, a hydrogen atom, alkyl or fluoroalkyl of 1 to 6 carbon atoms, cycloalkyl of 3 to 6 carbon atoms or acyl of 1 to 7 carbon atoms, or wherein $R^{68}$ and $R^{69}$ constitute a saturated hydrocarbon bridge of 3 to 5 carbon atoms which together with the nitrogen atom between them form a heterocyclic ring, and wherein one of $R^{68}$ and $R^{69}$ additionally is optionally the group $R^{59}$, (F) a group of the formula —$CONR^{70}R^{71}$, wherein $R^{70}$ and $R^{71}$ are each, independently, a hydrogen atom, alkyl or fluoroalkyl of 1 to 6 carbon atoms or cycloalkyl of 3 to 6 carbon atoms, or wherein $R^{70}$ and $R^{71}$ constitute a saturated hydrocarbon bridge of 3 to 5 carbon atoms which together with the nitrogen atom between them form a heterocyclic ring, and wherein one of $R^{70}$ and $R^{71}$ additionally is optionally the group $R^{59}$, (G) a group of the formula —$COR^{72}$, wherein $R^{72}$ is a hydrogen atom, straight or branched alkyl of 1 to 5 carbon atoms, cycloalkyl of 3 to 5 carbon atoms or $R^{59}$, (H) a group of the formula —OR$^{73}$, wherein R$^{73}$ is a hydrogen atom, an alkyl, fluoroalkyl or acyl group of 1 to 7 carbon atoms, or R$^{59}$, (I) a group of the formula —SR$^{74}$, wherein R$^{74}$ is a hydrogen atom, an alkyl, fluoroalkyl or acyl group of 1 to 7 carbon atoms, or R$^{59}$, (J) cyano, (K) nitro, or (L) halogen;

R$^5$ is Cl or trifluoromethyl;

Z is =N— or =CR$^6$— wherein R$^6$ is a hydrogen, fluorine, chlorine, bromine or iodine atom, methyl or trifluoromethyl; and, R$^7$ is a hydrogen, fluorine, chlorine, bromine or iodine atom, methyl, cyano, nitro or trifluoromethyl, with the condition that when Z is N or =CH—, R$^7$ is chlorine or trufluoromethyl;

and pharmaceutically acceptable salts thereof.

As the term is used herein, a "pharmaceutically acceptable counter ion" is any counter ion generally regarded by those skilled in the pharmaceutical art as being pharmaceutically acceptable. For a discussion of what are pharmaceutically acceptable counter ions, reference may be had to Stephen M. Bergle, Lyle D. Bighley and Donald C. Monkhouse, "Pharmaceutical Salts", *Journal of Pharmaceutical Sciences,* 66 (1977), 1–19. By way of non-limiting example, the chloride, bromide, acetate, and sulphate ions are pharmaceutically acceptable counter ions.

Preferred compounds of formula I are those wherein:

Y is an oxygen atom;

Z is an oxygen atom;

X is a divalent group of the formula >NR$^1$, wherein R$^1$ is:

(A) a hydrogen atom, (B) methyl or ethyl, or (C) —COCH$_3$

R$^2$ is:

(A) a hydrogen atom, or (B) methyl;

R$^3$ is a group of the formula —CH$_2$R$^{41}$, wherein R$^{41}$ is phenyl wherein one or more of the hydrogen atoms of said phenyl group are necessarily and independently replaced with:

(A) R$^{62}$, which is aryl selected from the group consisting of phenyl, or pyridyl, wherein one or more of the hydrogen atoms of said aryl group is optionally and independently replaced with:

(i) methyl, or (ii) halogen, (B) methyl, which is optionally mono- or polysubstituted with fluorine atoms, (C) a group of the formula —COR$^{78}$, wherein R$^{78}$ is methyl or R$^{62}$, (D) halogen;

R$^4$ is a chlorine atom;

R$^5$ is a hydrogen atom; and,

R$^6$ is a chlorine atom;

or a pharmaceutically acceptable salt thereof.

Preferred compounds of formula II are those wherein:

A$^1$ is =N—;

A$^2$ is =C(H)—;

D is =C(SO$_2$R$^1$)—, wherein R$^1$ is selected from the group consisting of:

(A) methyl, and (B) saturated heterocyclic groups selected from the group consisting of pyrrolidinyl, piperidinyl, piperazinyl and morpholinyl wherein said heterocyclic groups are optionally mono- or di-substituted with moieties independently selected from the group consisting of:

(i) oxo, (ii) —OR$^{101}$, wherein R$^{101}$ is:

(a) a hydrogen atom, (b) alkyl of 1 to 7 carbons, wherein one hydrogen atom of said alkyl group is optionally replaced with —OH, —OR$^{110}$ (wherein R$^{110}$ is an alkyl moiety of 1 to 6 carbon atoms), —NH$_2$, —NHMe or —NMe$_2$, or (c) acyl of 1 to 7 carbons, wherein one hydrogen atom of said acyl group is optionally replaced with —OH, —OR$^{111}$ (wherein R$^{111}$ is an alkyl moiety of 1 to 6 carbon atoms), —NH$_2$, —NHMe or —NMe$_2$, (iii) —CONR$^{105}$R$^{106}$, wherein R$^{105}$ and R$^{106}$ are each independently:

(a) a hydrogen atom, or (b) straight or branched alkyl of 1 to 7 atoms or cycloalkyl of 3 to 7 atoms, wherein said alkyl or cycloalkyl group is optionally monosubstituted with —OH, —OR$^{123}$ (wherein R$^{123}$ is an alkyl moiety of 1 to 6 carbon atoms), —NH$_2$, —NHMe, —NMe$_2$, pyrrolidinyl, piperidinyl, piperazinyl or morpholinyl, or, wherein R$^{105}$ and R$^{106}$ constitute a saturated hydrocarbon bridge of 3 to 5 carbon atoms which together with the nitrogen atom between them form a heterocyclic ring, and wherein one carbon atom in said hydrocarbon bridge is optionally replaced by —O—, —NH—, or —NMe—, (iv) —COOR$^{107}$, wherein R$^{107}$ is a hydrogen atom, or straight or branched alkyl of 1 to 7 carbon atoms, (v) straight or branched alkyl of 1 to 7 carbon atoms wherein one or two hydrogen atoms of said alkyl group are optionally replaced with moieties independently selected from the group consisting of:

(a) oxo, (b) —OH, (c) —OR$^{113}$, wherein R$^{113}$ is alkyl of 1 to 6 carbon atoms, (d) —OCOCH$_3$, (e) —NH$_2$, (f) —NHMe, (g) —NMe$_2$, (h) —CO$_2$H, and (i) —CO$_2$ R$^{114}$ wherein R$^{114}$ is alkyl of 1 to 3 carbon atoms, or cycloalkyl of 3 to 7 carbons, (vi) acyl of 1 to 7 carbon atoms, which is straight, branched or cyclic, and wherein one or two hydrogen atoms of said acyl group is optionally replaced with a moiety selected from the group consisting of:

(a) —OH, (b) —OR$^{115,}$ wherein R$^{115}$ is alkyl of 1 to 6 carbon atoms, (c) —NH$_2$, (d) —NHMe, (e) —NMe$_2$, (f) —NHCOMe, (g) oxo, (h) —CO$_2$ R$^{116}$, wherein R$^{116}$ is alkyl of 1 to 3 carbon atoms, (i) —CN, (j) the halogen atoms,
(k) heterocycles selected from the group consisting of pyrrolidinyl, piperidinyl, piperazinyl, morpholinyl and thiomorpholinyl, and
(l) aryl or heteroaryl selected from the group consisting of phenyl, thiophenyl, pyridyl, pyrimidinyl, furyl, pyrrolyl and oxazolyl, (vii) —SO$_2$R$^{108}$, wherein R$^{108}$ is:
(a) a heterocyclic group selected from the group consisting of pyrrolidinyl, piperidinyl, piperazinyl and morpholinyl wherein said heterocyclic group is optionally substituted with one moiety selected from the group consisting of straight or branched alkyl of 1 to 6 carbons, and —OR$^{118}$ (wherein R$^{118}$ is hydrogen or alkyl of 1 to 6 carbon atoms), (viii) —COR$^{109}$, wherein R$^{109}$ is:
(a) a heterocyclic group selected from the group consisting of pyrrolidinyl, piperidinyl, piperazinyl and morpholinyl wherein said heterocyclyl is optionally substituted with one halogen, straight or branched alkyl of 1 to 6 carbons, or —OR$^{121}$ (wherein R$^{121}$ is hydrogen or alkyl of 1 to 6 carbon atoms), and (ix) —CHO;

X is an oxygen atom;
R$^3$ is methyl;
R$^4$ is a group of the formula —CH$_2$R$^{55}$, wherein, R$^{55}$ is:
phenyl, which is optionally substituted at the 4-position with:
(A) R$^{59e}$, which is aryl or heteroaryl selected from the group consisting of phenyl, pyridyl, and pyrimidinyl
(B) —CN,
(B) nitro, or
(C) halogen;
R$^5$ is Cl;
Z is =C(H)—; and,
R$^7$ is Cl;
and pharmaceutically acceptable salts thereof.

Preferred compounds of formula III are those wherein:
A$^1$, A$^2$ and A$^3$ are each, independently, =N— or =CH—;
D is =N—, =CR$^1$—, =CSO$_2$R$^1$—, =CSOR$^1$—, =CSR$^1$—, =COR$^1$—, =CCOR$^1$—, or =CNHR$^1$—
wherein R$^1$ is:
(A) a hydrogen atom,
(B) branched or unbranched alkyl of 1 to 6 carbon atoms or cycloalkyl of 3 to 6 carbon atoms, which alkyl or cycloalkyl group is optionally mono- or polysubstituted with:
(i) halogen,
(ii) oxo,
(iii) aryl which is selected from the group consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl, wherein one or more hydrogen atoms of said aryl group is optionally and independently replaced with:
(a) alkyl of 1 to 3 carbon atoms,
(b) —COOH,
(c) —SO$_2$OH,
(d) —PO(OH)$_2$,
(e) a group of the formula —COOR$^8$, wherein R$^8$ is straight or branched alkyl of 1 to 5 carbon atoms or cycloalkyl of 3 to 5 carbon atoms,
(f) a group of the formula —NR$^9$R$^{10}$, wherein R$^9$ and R$^{10}$ are each independently a hydrogen atom, alkyl of 1 to 6 carbon atoms, cycloalkyl of 3 to 6 carbon atoms or acyl of 1 to 7 carbon atoms, or wherein R$^9$ and R$^{10}$ constitute a saturated hydrocarbon bridge of 3 to 5 carbon atoms which together with the nitrogen atom between them form a heterocyclic ring,
(g) a group of the formula —CONR$^{11}$R$^{12}$, wherein R$^{11}$ and R$^{12}$ are each independently a hydrogen atom, alkyl of 1 to 6 carbon atoms or cycloalkyl of 3 to 6 carbon atoms, or wherein R$^{11}$ and R$^{12}$ constitute a saturated hydrocarbon bridge of 3 to 5 carbon atoms which together with the nitrogen atom between them form a heterocyclic ring,
(h) a group of the formula —OR$^{13}$, wherein R$^{13}$ is a hydrogen atom, or an alkyl or acyl group of 1 to 7 carbon atoms,
(i) a group of the formula —SR$^{14}$, wherein R$^{14}$ is a hydrogen atom, or an alkyl or acyl group of 1 to 7 carbon atoms,
(j) cyano, or
(k) an amidino group of the formula:

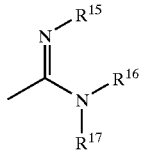

wherein R$^{15}$, R$^{16}$ and R$^{17}$ are each, independently, a hydrogen atom or alkyl of 1 to 3 carbon atoms, or wherein one of R$^{15}$, R$^{16}$ and R$^{17}$ is a hydrogen atom or alkyl of 1 to 3 carbon atoms and wherein the remaining two of R$^{15}$, R$^{16}$ and R$^{17}$ together form a saturated hydrocarbon bridge of 3 to 5 carbon atoms which together with the nitrogen atom(s) between them form a heterocyclic ring, (iv) a group of the formula —COOR$^{18}$, wherein R$^{18}$ is straight or branched alkyl of 1 to 7 carbon atoms or cycloalkyl of 3 to 6 carbon atoms,
(v) cyano,
(vi) a group of the formula —CONR$^{19}$R$^{20}$, wherein R$^{19}$ and R$^{20}$ are each, independently, a hydrogen atom, alkyl of 1 to 6 carbon atoms or cycloalkyl of 3 to 6 carbon atoms, or wherein R$^{19}$ and R$^{20}$ constitute a saturated hydrocarbon bridge of 3 to 5 carbon atoms which together with the nitrogen atom between them form a heterocyclic ring,
(vii) a group of the formula —OR$^{21}$, wherein R$^{21}$ is a hydrogen atom, or an alkyl or acyl group of 1 to 7 carbon atoms,
(viii) a group of the formula —SR$^{22}$, wherein R$^{22}$ is a hydrogen atom, or an alkyl or acyl group of 1 to 7 carbon atoms,
(ix) a group of the formula —NR$^{23}$R$^{24}$, wherein R$^{23}$ and R$^{24}$ are each, independently,
(a) a hydrogen atom,
(b) alkyl or acyl of 1 to 7 carbon atoms or cycloalkyl of 3 to 7 carbon atoms,
(c) a group of the formula —(CH$_2$)$_m$COOH, wherein m is 0, 1 or 2, or (d) a group of the formula —(CH$_2$)$_n$COOR$^{25}$, wherein n is 0, 1 or 2, wherein R$^{25}$ is straight or branched alkyl of 1 to 6 carbon atoms, or wherein R$^{23}$ and R$^{24}$ constitute a saturated hydrocarbon bridge of 3 to 5 carbon atoms which together with the nitrogen atom between them form a heterocyclic ring, or (x) a quaternary group of the formula:

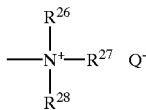

wherein R$^{26}$, R$^{27}$ and R$^{28}$ are each, independently, a branched or unbranched alkyl group of 1 to 7 carbon atoms and Q$^-$ is a chlorine, bromine or iodine counterion, (C) a branched or unbranched carboxylic acid group of 3 to 6 carbon atoms, (D) a branched or unbranched phosphonic acid group of 2 to 6 carbon atoms, (E) a branched or unbranched sulfonic acid group of 2 to 6 carbon atoms, (F) an amidino group of the formula:

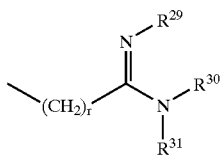

wherein r is 2, 3, 4, 5 or 6, and

R$^{29}$, R$^{30}$ and R$^{31}$ are each, independently, a hydrogen atom or alkyl of 1 to 3 carbon atoms, or wherein one of R$^{29}$, R$^{30}$ and R$^{31}$ is a hydrogen atom or alkyl of 1 to 3 carbon atoms and wherein the remaining two of R$^{29}$, R$^{30}$ and R$^{31}$ together form a saturated hydrocarbon bridge of 3 to 5 carbon atoms which together with the nitrogen atom(s) between them form a heterocyclic ring, (G) an guanidino group of the formula:

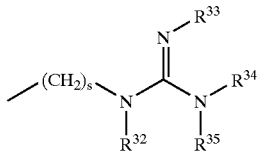

wherein s is 2, 3, 4, 5 or 6, and

R$^{32}$, R$^{33}$, R$^{34}$ and R$^{35}$ are each, independently, a hydrogen atom or alkyl of 1 to 3 carbon atoms, or wherein two of R$^{32}$, R$^{33}$, R$^{34}$ and R$^{35}$ are each, independently, a hydrogen atom or alkyl of 1 to 3 carbon atoms and wherein the remaining two of R$^{32}$, R$^{33}$, R$^{34}$ and R$^{35}$ together form a saturated hydrocarbon bridge of 3 to 5 carbon atoms which together with the nitrogen atom(s) between them form a heterocyclic ring, (H) aryl which is selected from the group consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl, wherein one or more hydrogen atoms of said aryl group is optionally and independently replaced with:

(i) alkyl of 1 to 3 carbon atoms, (ii) —COOH, (iii) —SO$_2$OH, (iv) —PO(OH)$_2$, (v) a group of the formula —COOR$^{36}$, wherein R$^{36}$ is straight or branched alkyl of 1 to 5 carbon atoms or cycloalkyl of 3 to 5 carbon atoms, (vi) a group of the formula —NR$^{37}$R$^{38}$, wherein R$^{37}$ and R$^{38}$ are each, independently, a hydrogen atom, alkyl of 1 to 6 carbon atoms, cycloalkyl of 3 to 6 carbon atoms or acyl of 1 to 7 carbon atoms, or wherein R$^{37}$ and R$^{38}$ constitute a saturated hydrocarbon bridge of 3 to 5 carbon atoms which together with the nitrogen atom between them form a heterocyclic ring, (vii) a group of the formula —CONR$^{39}$R$^{40}$, wherein R$^{39}$ and R$^{40}$ are each, independently, a hydrogen atom, alkyl of 1 to 6 carbon atoms or cycloalkyl of 3 to 6 carbon atoms, or wherein R$^{39}$ and R$^{40}$ constitute a saturated hydrocarbon bridge of 3 to 5 carbon atoms which together with the nitrogen atom between them form a heterocyclic ring, (viii) a group of the formula —OR$^{41}$, wherein R$^{41}$ is a hydrogen atom, or an alkyl or acyl group of 1 to 7 carbon atoms, (ix) a group of the formula —SR$^{42}$, wherein R$^{42}$ is a hydrogen atom, or an alkyl or acyl group of 1 to 7 carbon atoms, (x) cyano, or (xi) an amidino group of the formula:

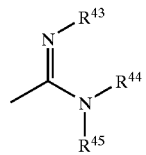

wherein R$^{43}$, R$^{44}$ and R$^{45}$ are each, independently, a hydrogen atom or alkyl of 1 to 3 carbon atoms, or wherein one of R$^{43}$, R$^{44}$ and R$^{45}$ is a hydrogen atom or alkyl of 1 to 3 carbon atoms and wherein the remaining two of R$^{43}$, R$^{44}$ and R$^{45}$ together form a saturated hydrocarbon bridge of 3 to 5 carbon atoms which together with the nitrogen atom(s) between them form a heterocyclic ring, (I) a group of the formula —NR$^{46}$R$^{47}$, wherein R$^{46}$ and R$^{47}$ are each independently a hydrogen atom, alkyl of 1 to 6 carbon atoms, cycloalkyl of 3 to 6 carbon atoms or acyl of 1 to 7 carbon atoms, or wherein R$^{46}$ and R$^{47}$ constitute a saturated hydrocarbon bridge of 3 to 5 carbon atoms which together with the nitrogen atom between them form a heterocyclic ring, (J) a morpholinyl moiety, or, (K) halogen;

X is an oxygen or sulfur atom;

$R^3$ is:
  (A) a hydrogen atom, or
  (B) branched or unbranched alkyl of 1 to 3 carbon atoms or cycloalkyl of 3 to 5 carbon atoms wherein said alkyl or cycloalkyl group is optionally substituted with:
    (i) a group of the formula —OR$^{48}$, wherein R$^{48}$ is a hydrogen atom, or an alkyl or acyl group of 1 to 7 carbon atoms, or
    (ii) a group of the formula —NR$^{49}$R$^{50}$, wherein R$^{49}$ and R$^{50}$ are each, independently, a hydrogen atom, alkyl of 1 to 2 carbon atoms, or acyl of 1 to 2 carbon atoms;

$R^4$ is a group of the formula —CH$_2$R$^{55}$, wherein:
  $R^{55}$ is:
    aryl selected from the group consisting of phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, -3, 6- or 7-indolyzinyl, 2-, 3-, 5- or 6-isoindolyl, 2- , 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-pthalaninyl, 2-, 3-, 6- or 7-quinoxalinyl, 2-, 3-, 6- or 7-napthyridinyl, 2-, 6- or 7-pteridinyl and 2-, 6- or 7-quinazolinyl, wherein one or more of the hydrogen atoms of said aryl group is optionally and independently replaced with:
      (A) R$^{59}$, which is aryl selected from the group consisting of phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, -3, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-pthalaninyl, 2-, 3-, 6- or 7-quinoxalinyl, 2-, 3-, 6- or 7-napthyridinyl, 2-, 6- or 7-pteridinyl and 2-, 6- or 7-quinazolinyl, wherein one or more of the hydrogen atoms of said aryl group is optionally and independently replaced with:
        (i) branched or unbranched alkyl of 1 to 6 carbon atoms or cycloalkyl of 3 to 6 carbon atoms, which alkyl or cycloalkyl group is optionally mono- or polysubstituted with halogen or oxo,
        (ii) cyano,
        (iii) nitro, or
        (iv) halogen,
      (B) methyl, which is optionally mono- or polysubstituted with fluorine atoms and additionally is optionally monosubstituted with R$^{59}$,
      (C) branched or unbranched alkyl of 2 to 6 carbon atoms or cycloalkyl of 3 to 6 carbon atoms, which alkyl or cycloalkyl group is optionally mono- or polysubstituted with halogen or oxo,
      (D) a group of the formula —COOR$^{67}$, wherein R$^{67}$ is straight or branched alkyl of 1 to 5 carbon atoms or cycloalkyl of 3 to 5 carbon atoms,
      (E) a group of the formula —NR$^{68}$R$^{69}$, wherein R$^{68}$ and R$^{69}$ are each, independently, a hydrogen atom, alkyl or fluoroalkyl of 1 to 6 carbon atoms, cycloalkyl of 3 to 6 carbon atoms or acyl of 1 to 7 carbon atoms, or wherein R$^{68}$ and R$^{69}$ constitute a saturated hydrocarbon bridge of 3 to 5 carbon atoms which together with the nitrogen atom between them form a heterocyclic ring, and wherein one of R$^{68}$ and R$^{69}$ may additionally be the group R$^{59}$,
      (F) a group of the formula —CONR$^{70}$R$^{71}$, wherein R$^{70}$ and R$^{71}$ are each, independently, a hydrogen atom, alkyl or fluoroalkyl of 1 to 6 carbon atoms or cycloalkyl of 3 to 6 carbon atoms, or wherein R$^{70}$ and R$^{71}$ constitute a saturated hydrocarbon bridge of 3 to 5 carbon atoms which together with the nitrogen atom between them form a heterocyclic ring, and wherein one of R$^{70}$ and R$^{71}$ additionally is optionally the group R$^{59}$,
      (G) a group of the formula —COR$^{72}$, wherein R$^{72}$ is a hydrogen atom, straight or branched alkyl of 1 to 5 carbon atoms, cycloalkyl of 3 to 5 carbon atoms or R$^{59}$,
      (H) a group of the formula —OR$^{73}$, wherein R$^{73}$ is a hydrogen atom, an alkyl, fluoroalkyl or acyl group of 1 to 7 carbon atoms, or R$^{59}$,
      (I) a group of the formula —SR$^{74}$, wherein R$^{74}$ is a hydrogen atom, an alkyl, fluoroalkyl or acyl group of 1 to 7 carbon atoms, or R$^{59}$,
      (J) cyano,
      (K) nitro, or
      (L) halogen;

$R^5$ is Cl or trifluoromethyl;

Z is =N— or =CR$^6$— wherein R$^6$ is a hydrogen, fluorine, chlorine, bromine or iodine atom, methyl or trifluoromethyl; and, $R^7$ is a hydrogen, fluorine, chlorine, bromine or iodine atom, methyl, cyano, nitro or trifluoromethyl, with the condition that when Z is N or =CH—, R$^7$ is chlorine or trufluoromethyl;

and pharmaceutically acceptable salts thereof.

The molecules of the invention can be screened for ability to bind or modify the R7.1 epitope of LFA-1 using techniques known in the art, including but not limited to competitive binding and non-competitive assay systems such as radioimmunoassays, ELISA, immunofluorescence assays, etc. For example, a test molecule can be screened against mAb R7.1 in a competitive immunofluorescence assay. One molecule that cross-competes with R7.1 (i.e., binds to the same to similar epitope) is R3.1 (data not shown).

The molecules that specifically bind or modify the R7.1 epitope of LFA-1 may be labeled with various compounds known in the art, including but not limited to: enzymes, radioisotopes, fluorescent compounds. The labeling and detection methods employed herein may, for example, be such as those described in Harlow and Lane (Harlow and Lane, 1988, Antibodies: A Laboratory Manual, Cold Spring Harbor Laboratory Press, Cold Spring Harbor, N.Y.).

Enzymes which can be used to label the molecules described herein include, inter alia, biotin, horseradish peroxidase, alkaline phosphatase. The detection can be accomplished by colorimetric methods which employ a chromogenic substrate for the enzyme. Detection may also be accomplished by visual comparison of the extent of enzymatic reaction of a substrate in comparison with similarly prepared standards.

Radioisotopes which can be used to label the molecules described herein include, inter alia, $^{125}$I, $^{131}$I, $^3$H. Such labeled molecules can be detected in in vitro assays using a radioimmunoassay (RIA) or radioprobe by means such as the use of a gamma counter or a scintillation counter or by autoradiography.

For use in the detection methods of the invention, the molecules are preferably labeled with a fluorescent compound, for example, Oregon Green® 488-X, succinimidyl ester 6-isomer (Molecular Probes, Inc., Eugene Oreg.). When the fluorescently labeled molecule is exposed to light of the proper wavelength, its presence can then be detected due to fluorescence by means such as a fluorescence microscope or flow activated cell sorting system (e.g., FACScan). Among the most commonly used fluorescent labeling compounds are fluorescein isothiocyanate (FITC), rhodamine, phycoerythrin (PE), phycocyanin, allophycocyanin, o-phthaldehyde, and fluorescamine.

In another aspect, the molecules of the invention may be detected using a labeled molecule that binds such molecules. The label may be selected from those described above. For example, R7.1 may be detected using a goat-anti-mouse IgG-PE conjugate.

For the receptor occupancy methods of the invention, a test molecule is administered to a subject. The subject is an animal, including but not limited to a mammal (e.g., cats, dogs, old and new world monkeys, humans). In a preferred embodiment, the subject is a human.

The methods of the invention can be used in formulating a range of dosage of the test compound for use in humans.

The invention also provides kits comprising one or more containers filled with one or more of the molecules of the invention.

The invention is further described in the following examples which are in no way intended to limit the scope of the invention.

EXAMPLES

In its first aspect, the invention comprises a method for identifying a molecule that specifically binds or modifies the R7.1 epitope of LFA-1.

Molecular Assay to Identify Molecules that Bind LFA-1

Purpose of Assay

This assay protocol was designed to develop a method for identifying molecules that inhibit the binding of purified LFA-1 to a molecule that specifically binds or modifies the R7.1 epitope of LFA-1.

Example 1

LFA-1 was purified using the TS2/4 mAb (American Type Culture Collection; Manassas, Va.) from a 20 g pellet of human JY or SKW3 cells, utilizing a protocol previously described (Dustin, M. J. et al., 1992, J. Immunol. 148:2654–2660). The LFA-1 was purified from SKW3 lysates by immunoaffinity chromatography on TS2/4 LFA-1 mAb Sepharose and eluted at pH 11.5 in the presence of 2 mM $MgCl_2$ and 1% octylglucoside. After collection and neutralization of fractions from the TS2/4 column, samples were pooled and precleared with Protein G agarose.

Micellar LFA-1 (50 µl) was immobilized onto a microtiter plate by adsorption at approximately 3 µg/ml in assay buffer (AB: dPBS+2 mM $Mg^{++}$) for 1 hr at room temperature. Non-specific sites were then blocked for 30 min with 2% BSA-AB. Various purified mAbs (50 µl at 10 µg/ml) (CLB-LFA-1, Research Diagnostics Inc., Flanders, N.J.; R7.1 and R3.1, generated at Boehringer Ingelheim Pharmaceuticals, Inc. (BIPI), Ridgefield, Conn.; MHM 24, Biomedia, Foster City, Calif.; TS 2/4 and T/S 1/22, American Type Culture Collection, Manassas, Va.; and mAb38, Research Diagnostics Inc., Flanders, N.J.) and 50 µl of Compound 1 ((R)-5-(4-bromobenzyl)-3-(3,5-dichlorophenyl)-1,5-dimethylimidazolidine-2,4-dione) or its enantiomer (Compound 2; 5 µM in AB) or dimethyl sulfoxide (DMSO) were then added and allowed to bind for 1 hour at 37° C. The plate was then washed 4 times and 50 µl of a goat anti-mouse-horseradish peroxidase (HRP) conjugate (Zymed, South San Francisco, Calif.) was added at a 1/4000 dilution in 1% BSA-AB. After 20 min at 37° C., the plate was washed as above and 200 µl of azino-bis(3-ethylbenzthiazoline-6-sulfonic acid) (ABTS) reagent (Zymed, South San Francisco, Calif.) was added to visualize binding. After approximately 15 min, absorbance was measured at 405 nm. Bars represent the mean of duplicate wells±the standard error.

Results

FIG. 1 shows that Compound 1, but not its enantiomer or a DMSO control, significantly inhibited the binding of R3.1 and R7.1 to purified LFA-1. As discussed above, R3.1 and R7.1 cross-compete, i.e., bind to the same or similar epitope (data not shown). Compound 1 did not inhibit the binding of the other anti-LFA mAbs.

Cellular Assays to Identify Molecules that Bind LFA-1

Purpose of Assays

This assay protocol (exemplified in Examples 2–4) was designed to identify molecules that inhibit the binding of cell surface LFA-1 to a molecule that specifically binds or modifies LFA-1. This assay may also be used to determine LFA-1 receptor occupancy on target cells treated with a molecule that specifically binds LFA-1 as described below in Example 5.

Example 2

SKW-3 Cells

Using flow cytometry, the binding of R3.1 to SKW-3 cells, a T-cell lymphoma that expresses high amounts of LFA-1, was assessed. After washing and counting, 100 µl of SKW-3 cells (1×10$^7$ cells/ml) were incubated with 13.3 nM mAb38 or R3.1 or R15.7 (generated at BIPI, Ridgefield, Conn.) and 10 µM Compound 1 or DMSO (0.09%) (negative control) for 30 minutes at 37° C. After centrifugation and 2 washes in HBSS (GIBCO, Grand Island, N.Y.), cells were incubated with a goat anti-mouse IgG-PE conjugate (Biosource International, Camarillo, Calif.) (diluted 1:50 in dPBS) for 20 minutes at 4° C. After 2 washes in dPBS, cells were fixed with 500 µl 1% paraformaldehyde and analyzed on a FACScan (Becton Dickinson, San Jose, Calif.).

Results

Figure 2:
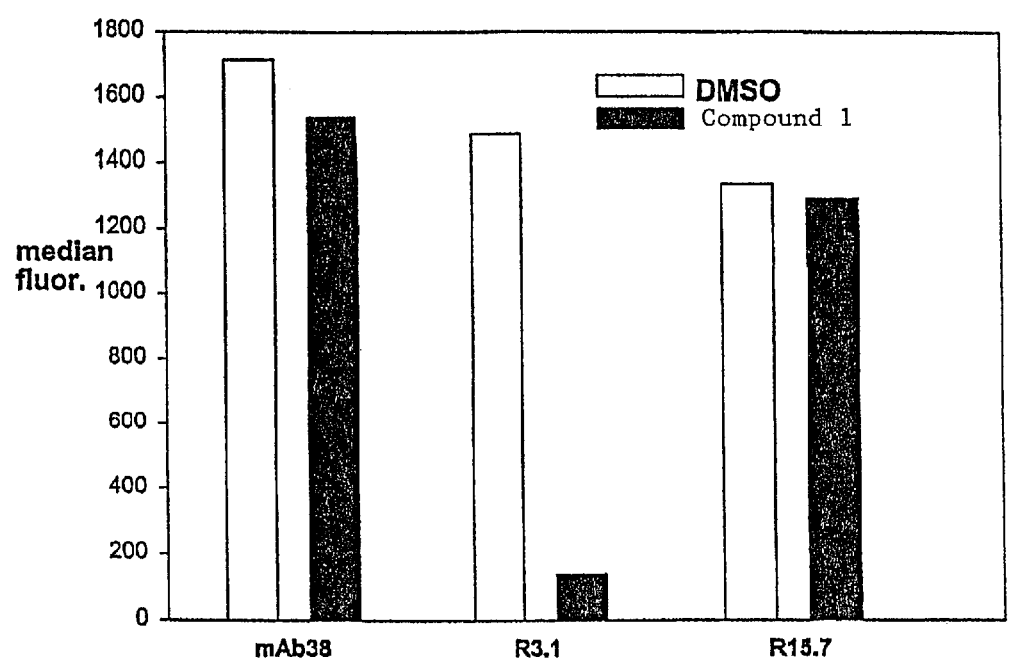
FIG. 2. Inhibition of mAb binding to SKW-3 cells by Compound 1. SKW-3 cells were incubated with an anti-LFA-1 mAb (mAb38 or R3.1; 13.3 nM) or an anti-CD18 mAb (mAb 15.7, 13.3 nM) in the presence of Compound 1 (10 $\mu$M) or a DMSO control (0.09%). Median fluorescence was assessed using flow cytometry.

FIG. 2 shows that Compound 1 but not DMSO inhibited the binding of R3.1 to the cell-bound LFA-1. Similar to the molecular assay described in Example 1, Compound 1 did not inhibit the binding of mAb38, another I domain binding mAb) or the anti-CD 18 mAb, R15.7 (Smith et al., 1989, J. Clin. Invest. 83(6):2008–2017).

Example 3

Human Whole Blood Cells

Using flow cytometry, the binding of R3.1 to human whole blood cells was assessed. Peripheral blood was obtained from normal healthy donors by venipuncture. R3.1 (3.3 nM) or R7.1 (3.3 nM) and various dilutions of Compound 1 or DMSO (0.2%) were incubated with 100 µl of human whole blood for 20 minutes at 4° C. After centrifugation and 1 wash in dPBS, the cells were then incubated with a goat anti-mouse IgG-PE conjugate (Biosource International, Camarillo, Calif.) diluted 1:50 in dPBS. After incubation in secondary reagent for 15 minutes at 4° C., cells were lysed and fixed in 100 µl of lysis buffer (Immunotech, Westbrook, Me.) for 10 min at room temperature and then 1 ml of water was added to each sample before analysis on a FACScan (Becton Dickinson, San Jose, Calif.).

Results

Figure 3:
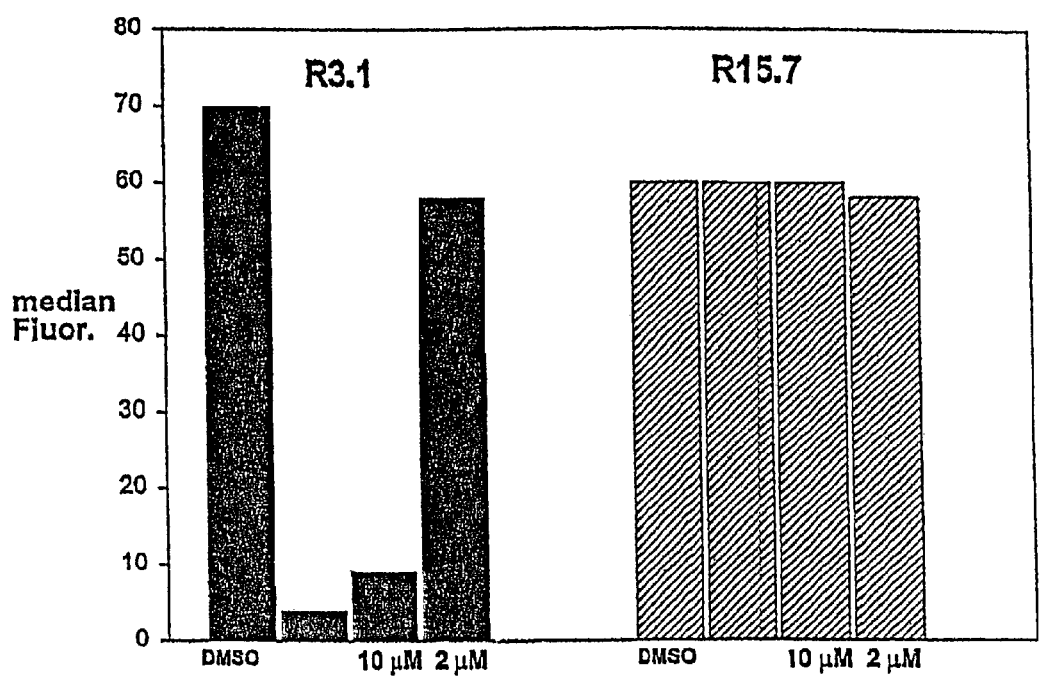
FIG. 3. Dose dependent inhibition of mAb binding to human leukocytes by Compound 1. Human whole blood was incubated with a mAb (R3.1 or R15.7; 3.3 nM) and Compound 1 (10 $\mu$M or 2 $\mu$M) or a DMSO control (0.2%). Median fluorescence was assessed using flow cytometry.

FIG. 3 shows that Compound 1, but not DMSO, inhibited the binding of R3.1 to leukocytes in a dose dependent manner. The same concentrations of compound did not inhibit the binding of the anti-CD18 mAb R15.7.

Example 4

Inhibition of Binding of Fab Fragments

Using flow cytometry, the inhibition of binding of R3.1 Fab fragments to human whole blood cells by a small molecule (Compound) such as that described in: U.S. patent application Ser. No. 09/375,010 by Kelly et al., filed Aug. 16, 1999; U.S. patent application Ser. No. 09/604,312 by Kelly et al., filed Jun. 27, 2000; and U.S. patent application Ser. No. 09/605,584 by Kelly et al., filed Jun. 28, 2000 is assessed.

R3.1 Fab fragments are generated by papain digestion: R3.1 is dialyzed into 0.1M sodium phosphate (EM Sciences), 50 mM sodium chloride (EM Sciences), pH 7.2 buffer (PBS). The concentration of the antibody is adjusted to between 1–5 mg/ml and 5 mM L-cysteine (Sigma, St. Louis, Mo.) is added to the antibody solution. Papain (Sigma, St. Louis, Mo.) is added immediately afterwards in 1:40 w/w (Ab:papain). After mixing well, the solution is incubated in a 37° C. water bath for 2–3 hours. 0.2 mM iodoacetamide in 5–10 ml of PBS is added to the AB solution which is then incubated for 30 min. The fragments are analyzed under reduced and non-reduced SDS-PAGE (polyacrylamide gel electrophoresis).

The Fab fragments are separated from the Fc portion using Protein A affinity chromatography (ProSepA, Bioprocessing, Inc., Scarborough, Me.) followed by anion exchange chromatography (DEAE Sepharose Fast Flow resin, Pharmacia). Following anion exchange, the Fab fragment solution is concentrated using the Amicon Filtron system (Millipore) with 10 Kd Diaflo ultrafiltration membranes. Amino acid analysis is performed to determine the concentration of Fab (Yale Biotechnology Center, New Haven, Conn.).

The R3.1 Fab fragments are labeled with Alexa 488® according to manufacturer's instructions (Molecular Probes, Inc., Eugene, Oreg.).

Peripheral blood is obtained from normal healthy donors by venipuncture. R3.1 Fab fragments labeled with Alexa 488® (10 nM) and various dilutions of Compound or Fab fragments (10 nM) in the absence of compound are incubated with 100 µl of human whole blood for 20 minutes at 4° C. After centrifugation and 1 wash in dPBS, the cells are lysed and fixed in 100 µl of lysis buffer (Immunotech, Westbrook, Me.) for 10 min at room temperature and then 1 ml of water is added to each sample before analysis on a FACScan (Becton Dickinson, San Jose, Calif.).

Example 5

A test compound is administered orally, intramucosally or parenterally to a subject. Peripheral blood is withdrawn from the subject at various time points post-administration of the test compound. A molecule that specifically binds or modifies the R7.1 epitope of LFA-1 is added to the blood and incubated for 20 minutes at 4° C. After centrifugation and one wash in dPBS, the cells are then incubated with a goat anti-mouse IgG-PE conjugate (Biosource International, Camarillo, Calif.) diluted 1:50 in dPBS. After incubation in secondary reagent for 15 minutes at 4° C., cells are lysed and fixed in 100 µl of lysis buffer (Immunotech, Westbrook, Me.) for 10 min at room temperature and then 1 ml of water is added to each sample before analysis on a FACScan (Becton Dickinson, San Jose, Calif.).

The present invention is not to be limited in scope by the specific embodiments described herein, which are intended as single illustrations of individual aspects of the invention, and functionally equivalent methods and components are within the scope of the invention.

Indeed, various modifications of the invention, in addition to those shown and described herein will become apparent to those skilled in the art from the foregoing description and accompanying drawings. Such modifications are intended to fall within the scope of the appended claims.

Various patent applications and publications are cited herein, the disclosures of which are incorporated by reference in their entireties.

What is claimed is:

1. A method for determining LFA-1 receptor occupancy comprising:
   (a) administering a first molecule to a subject;
   (b) withdrawing a sample of blood from the subject;
   (c) incubating the sample with a second molecule that specifically binds the R7.1 epitope of LFA-1, wherein the second molecule comprises a label; and
   (d) detecting the amount of the second molecule bound to the R7.1 epitope of LFA-1,
   wherein a decrease in the amount of binding of the second molecule indicates binding of the first molecule to LFA-1.

2. A method for determining LFA-1 receptor occupancy comprising:
   (a) administering a first molecule to a subject;
   (b) withdrawing a sample of blood from the subject;
   (c) incubating the sample with a second molecule that specifically binds the R7.1 epitope of LFA-1;
   (d) incubating the sample with a third molecule, wherein the third molecule binds the second molecule, and wherein the third molecule comprises a label; and
   (e) detecting the amount of the third molecule bound to the second molecule,
   wherein a decrease in the amount of binding of the third molecule indicates binding of the first molecule to LFA-1 such that binding of the second molecule to the R7.1 epitope of LFA-1 is decreased.

3. The method according to claim 1 or 2 wherein the second molecule is a monoclonal antibody or a fragment thereof.

4. The method according to claim 3 wherein the monoclonal antibody is R7.1.

5. The method according to claim 1 or 2 wherein the second molecule is a compound of the formula I.

6. The method according to claim 1 or 2 wherein the second molecule is a compound of the formula II.

7. The method according to claim 1 or 2 wherein the second molecule is a compound of the formula III.

8. The method according to claim 1 or 2 wherein the subject is a human.

9. The method of claim 1 or 2 wherein the label is a fluorescent compound.

* * * * *